(12) United States Patent
Ray et al.

(10) Patent No.: US 9,577,596 B2
(45) Date of Patent: Feb. 21, 2017

(54) SYSTEM AND METHOD FOR PERSONALIZATION OF AN AUDIO EQUALIZER

(71) Applicant: Sound Innovations Inc., White River Junction, VT (US)

(72) Inventors: Laura E. Ray, Hanover, NH (US); Jason A. Solbeck, White River Junction, VT (US); Christopher M. Pearson, White River Junction, VT (US)

(73) Assignee: SOUND INNOVATIONS, LLC, Simpson, PA (US)

( * ) Notice: Subject to any disclaimer, the term of this patent is extended or adjusted under 35 U.S.C. 154(b) by 584 days.

(21) Appl. No.: 13/790,254

(22) Filed: Mar. 8, 2013

(65) Prior Publication Data

US 2014/0254828 A1    Sep. 11, 2014

(51) Int. Cl.
  *H03G 5/16* (2006.01)
  *H03G 5/00* (2006.01)
  *H04R 25/00* (2006.01)
  *A61B 5/12* (2006.01)

(52) U.S. Cl.
  CPC .............. *H03G 5/165* (2013.01); *A61B 5/123* (2013.01); *H03G 5/005* (2013.01); *H04R 25/70* (2013.01)

(58) Field of Classification Search
  CPC ........ H03G 5/165; H03G 5/005; H04R 25/70; A61B 5/123
  See application file for complete search history.

(56) References Cited

U.S. PATENT DOCUMENTS

| | | | |
|---|---|---|---|
| 6,201,875 B1 * | 3/2001 | Davis | H04R 25/70 381/314 |
| 8,054,993 B1 * | 11/2011 | Kreifeldt | H03G 9/005 381/101 |
| 2002/0111745 A1 | 8/2002 | Bye et al. | 702/19 |
| 2004/0184618 A1 | 9/2004 | Bengtsson | 381/60 |
| 2004/0240696 A1 | 12/2004 | Shively et al. | 381/331 |

(Continued)

FOREIGN PATENT DOCUMENTS

WO   WO 2012/033942   3/2012   .............. H03G 5/00

*Primary Examiner* — Davetta W Goins
*Assistant Examiner* — Daniel Sellers
(74) *Attorney, Agent, or Firm* — Morgan, Lewis & Bockius LLP

(57) ABSTRACT

The invention is directed to synthesizing a personalized audio equalization filter based on an individual's hearing profile when listening to audio signals using a preferred electronic means of transduction and production of the audio signals through headphones, earphones, or loudspeakers and is presented in two steps. In the first step, the deviation of the listener's hearing profile, when the preferred listening device is donned, is measured and recorded relative to predetermined equal-loudness contours (e.g., ISO standard equal-loudness contours). The hearing profile is used to compute an equalization filter such that when the audio signal to be reproduced is played through the filter, the equal-loudness contour for a specified phon level is restored. Thus, the invention compensates for deviations of the user's listening device, the user's own hearing profile from a standard hearing profile that represents natural hearing, and other factors. The equalization filter can be adapted to any phon level through adaptation of filter coefficients as a function of the volume of the listening level.

22 Claims, 19 Drawing Sheets

(56) References Cited

U.S. PATENT DOCUMENTS

| | | |
|---|---|---|
| 2005/0013445 A1* | 1/2005 | Martin ............................ 381/60 |
| 2006/0045281 A1 | 3/2006 | Korneluk et al. .............. 381/60 |
| 2007/0204694 A1 | 9/2007 | Davis ............................. 73/585 |
| 2007/0223752 A1* | 9/2007 | Boretzki ................ H04R 25/70 381/312 |
| 2007/0270988 A1* | 11/2007 | Goldstein et al. .............. 700/94 |
| 2007/0282393 A1 | 12/2007 | Marquis ......................... 607/55 |
| 2007/0297634 A1* | 12/2007 | Hansson ...................... 381/384 |
| 2009/0074216 A1 | 3/2009 | Bradford et al. ............. 381/315 |
| 2010/0119093 A1* | 5/2010 | Uzuanis et al. ............. 381/312 |
| 2011/0002471 A1* | 1/2011 | Wihardja et al. ............... 381/56 |
| 2011/0299709 A1* | 12/2011 | Anderson et al. ........... 381/315 |
| 2012/0063616 A1* | 3/2012 | Walsh et al. ................. 381/103 |

* cited by examiner

SYSTEM AND METHOD FOR PERSONALIZATION OF AN AUDIO EQUALIZER

FIELD OF THE INVENTION

The invention is directed to synthesizing a personalized audio equalization filter based on an individual's hearing profile when listening to audio signals using a preferred electronic means of transduction and production of the audio signals through headphones, earphones, or loudspeakers.

BACKGROUND OF THE INVENTION

When an audio signal is reproduced for listening such as through speakers or headphones, the resulting audio signal and the listener's perception of the audio signal depend on a number of factors, including such things as the listener's hearing profile, the frequency response of the device used for transduction and production of the audio signals, and other factors (e.g., the listening environment, including noise, room acoustics, different levels of attenuation at different frequencies, etc.). Audio signals are often equalized in order to compensate for some of these factors. Equalization alters the frequency response of an audio signal reproduced using an electronic means of transduction by filtering of the audio signal. For example, if the listener has hearing loss in certain audio bands, signals in these bands can be amplified to recreate natural listening conditions intended for the audio signal.

Each listener's hearing profile differs depending on various factors, such as age, psychoacoustic factors, existence of hearing loss, and if present, type of hearing loss. Furthermore, a variety of devices exist for listening, including in-the-ear earphones that seal the ear from external noise, earbuds that are placed in the ear but do not provide a seal, circumaural or over-the-ear devices, supra-aural or on-the ear devices, open-back devices, and stereo speakers, to name but a few, plus the related devices that process and amplify the audio signal, including MP3 players, smartphones, pad computers, laptop computers, desktop computers, stereo receivers, and other similar devices. The frequency response of the signal path between the receiver of the listening device and the listener's tympanic membrane also varies and is dependent on the frequency response of the listening device and the volume of air in the signal path. The frequency response of this signal path therefore varies from listener to listener. The electronic amplifier used to deliver power for transduction of the audio signal also has a characteristic frequency response. Thus, each of the devices within a system that reproduces an audio signal for listening has a unique characteristic frequency response that shapes the audio signal being reproduced as does the listener's hearing profile and listener-listening device combination.

Prior art provides equalization based on a standard audiogram, which is a threshold hearing level test that is performed using specialized audio equipment in an audiometric booth. Specifically, the threshold of hearing is established through presentation of pure tones and listener indication of whether the tone is heard at each frequency. The threshold at which each tone is heard at each frequency establishes the audiogram. The zero phon (threshold) level equal-loudness contour may be used to provide an equalization filter to enhance hearing. However, in the context of personalized audio listening, measuring the audiogram requires an environment with a very low noise floor, such as an audiometric booth, and external noise influences the accuracy of threshold determination significantly. Moreover, audiograms are generally performed with a specified listening device, and not the listening device preferred by the user for personal use in listening to audio. Furthermore, it is well-known that the frequency response of human hearing is itself a function of sound pressure level, and thus that the sensitivity of hearing is strongly frequency- and level-dependent. As such, audiometric testing provides only a single measure of frequency response of human hearing—at threshold. Since listening generally does not occur at threshold, the equalization filter generated through threshold tests provides an inadequate representation of equalization needed at higher listening volumes to restore an equalized signal providing natural listening matched to a specified equal-loudness contour.

SUMMARY OF EXEMPLARY EMBODIMENTS

In one embodiment there is provided a method for automatically generating a personalized equalization filter for listener. The method involves measuring a first hearing profile of the listener as a deviation of a first recorded response profile, obtained from a first equal loudness hearing test when the listener is listening through a personal listening device in a personal listening environment, from a first reference equal-loudness contour associated with a first given phon level (e.g., an equal-loudness contour specified by ISO 226:2003); automatically generating a first personalized equalization filter based on the measured deviation of the first hearing profile such that application of the personalized equalization filter to an audio signal played through the personal listening device provides an equalized listening profile that recovers the equal-loudness contour for which the hearing profile was measured; and applying the first personalized equalization filter to an audio signal played through the personal listening device.

In various alternative embodiments, measuring the first hearing profile of the listener may involve conducting a first equal loudness hearing test including presenting a user interface to the listener, the user interface providing a first set of test tones and allowing the listener to adjust and set the relative volume level of each test tone to a level at which the listener perceives all of the tones to be at the same loudness for the given phon level; recording a phon level set by the listener for each test tone to produce the first recorded response profile; and measuring the hearing profile of the listener as a deviation of the first recorded response profile from the reference equal-loudness contour at the given phon level. The first hearing test may be conducted in a manner that does not require a quiet environment with low noise floor.

Furthermore, automatically generating the first personalized equalization filter may involve automatically creating a first digital equalization filter using a set of parametric equalizing filters by automatically specifying the center frequency, bandwidth, and desired amplification or attenuation, based on the difference between the listener's measured contour and the reference contour and cascading filters for each band to provide a personalized equalization filter.

The method may further involve automatically adapting the personalized equalization filter to a new phon level that differs from the phon level for which the listener's hearing profile was measured so that the personalized equalization filter automatically adapts to match an equal-loudness contour of the new phon level. In certain embodiments, automatically adapting the personalized equalization filter may involve automatically adapting the personalized equalization filter based on a second recorded response profile and a second reference equal-loudness contour associated with a second given phon level, which may be done, for example, by measuring a second hearing profile of the listener as a deviation of the second recorded response profile from the second reference equal-loudness contour, automatically generating a second personalized equalization filter based on the measured deviation of the first hearing profile, and generating a third personalized equalization filter by deriving coefficients for the third personalized equalization filter based on coefficients for the first and second personalized equalization filters. In other embodiments, automatically adapting the personalized equalization filter may involve automatically adapting the personalized equalization filter based on a database containing frequency responses of various listening devices.

In any of the above embodiments, the method may further involve automatically adjusting the personalized equalization filter based on a head-related transfer function to allow one or more audio signals to be perceived as coming from different directions in three dimensional space and/or automatically adjusting the personalized equalization filter to emphasize or de-emphasize audio signals within a specified band.

In any of the above embodiments, the personal listening device may include an internal microphone for determining a fit of the personal listening device on the listener, and, upon determining that the fit of the personal listening device on the listener has changed, the method may further involve automatically adjusting the personalized equalization filter based on a transfer function associated with the fit of the device and/or automatically prompting the listener to conduct a hearing test due to the change in fit.

In another embodiment there is provided apparatus for automatically generating a personalized equalization filter for a listener, where the apparatus includes a hearing test module configured to produce a first recorded response profile from a first equal loudness hearing test when the listener is listening through a personal listening device in a personal listening environment and also includes an adaptive equalization filter module configured to measure a first hearing profile of the listener as a deviation of the first recorded response profile from a first reference equal-loudness contour associated with a first given phon level (e.g., an equal-loudness contour specified by ISO 226:2003), automatically generate a first personalized equalization filter based on the measured deviation of the first hearing profile such that application of the personalized equalization filter to an audio signal played through the personal listening device provides an equalized listening profile that recovers the equal-loudness contour for which the hearing profile was measured, and apply the first personalized equalization filter to an audio signal played through the personal listening device.

In various alternative embodiments, the hearing test module may be configured to conduct a first equal loudness hearing test including presenting a user interface to the listener, the user interface providing a first set of test tones and allowing the listener to adjust and set the relative volume level of each test tone to a level at which the listener perceives all of the tones to be at the same loudness for the given phon level and record a phon level set by the listener for each test tone to produce the first recorded response profile. The hearing test module may be configured to conduct the first hearing test in a manner that does not require a quiet environment with low noise floor.

Furthermore, the adaptive equalization filter module may be configured to automatically generate the first personalized equalization filter by automatically creating a first digital equalization filter using a set of parametric equalizing filters by automatically specifying the center frequency, bandwidth, and desired amplification or attenuation, based on the difference between the listener's measured contour and the reference contour and cascading filters for each band to provide a personalized equalization filter.

The adaptive equalization filter module may be further configured to automatically adapt the personalized equalization filter to a new phon level that differs from the phon level for which the listener's hearing profile was measured so that the personalized equalization filter automatically adapts to match an equal-loudness contour of the new phon level. In certain embodiments, the adaptive equalization filter module may be configured to automatically adapt the personalized equalization filter based on a second recorded response profile and a second reference equal-loudness contour associated with a second given phon level, which may be done, for example, by measuring a second hearing profile of the listener as a deviation of the second recorded response profile from the second reference equal-loudness contour, automatically generating a second personalized equalization filter based on the measured deviation of the first hearing profile, and generating a third personalized equalization filter by deriving coefficients for the third personalized equalization filter based on coefficients for the first and second personalized equalization filters. In other embodiments, the adaptive equalization filter module may be configured to automatically adapt the personalized equalization filter by automatically adapting the personalized equalization filter based on a database containing frequency responses of various listening devices.

In any of the above embodiments, the adaptive equalization filter module may be configured to automatically adjust the personalized equalization filter based on a head-related transfer function to allow one or more audio signals to be perceived as coming from different directions in three dimensional space and/or automatically adjust the personalized equalization filter to emphasize or de-emphasize audio signals within a specified band.

In any of the above embodiments, the personal listening device may include an internal microphone for determining a fit of the personal listening device on the listener, and, upon determining that the fit of the personal listening device on the listener has changed, the adaptive equalization filter module may be configured to automatically adjust the personalized equalization filter based on a transfer function associated with the fit of the device and/or automatically prompt the listener to conduct a hearing test due to the change in fit.

In any of the above embodiments, the hearing test module and the adaptive equalization filter module may be integral to a device including at least one of a computer, cell phone, portable music player, tablet computer, laptop computer, notebook computer, desktop computer, stereo receiver, or programmable device. Alternatively, the hearing test module and an adaptive equalization filter generator of the adaptive equalization filter module may be integral to a first device and an equalization filter of the adaptive equalization filter module may be integral to a second device used in conjunction with the first device, wherein the second device includes at least one component providing additional signal processing of the audio signal, the second device being programmable through the first device to incorporate the personalized equalization filter and apply the personalized equalization filter to the audio signal in conjunction with at least one additional signal processing function. The second device may include an electronic component for providing additional signal processing of the audio signal, a digital signal processor for providing additional signal processing of the audio signal, and/or a microprocessor for providing additional signal processing of the audio signal. The additional signal processing function may include such things as radio communication, talk-through, active noise reduction, in-ear voice pickup, and/or impulse suppression.

Additional embodiments may be disclosed and claimed.

BRIEF DESCRIPTION OF THE DRAWINGS

The foregoing features of embodiments will be more readily understood by reference to the following detailed description, taken with reference to the accompanying drawings, in which.

It should be noted that the foregoing figures and the elements depicted therein are not necessarily drawn to consistent scale or to any scale. Unless the context otherwise suggests, like elements are indicated by like numerals.

DETAILED DESCRIPTION OF SPECIFIC EMBODIMENTS

Embodiments of the present invention are directed to systems and methods for establishing and applying an adaptive, personalized equalization filter for audio listening having three major components: (1) a methodology for measuring hearing profile with respect to deviation from equal-loudness contours at one or more phon levels when a personal listening device is used to reproduce the audio signal in a personal listening environment (as opposed to determining a hearing profile using an audiogram technique using specialized audio equipment in a quiet environment with low noise floor such as an audiometric booth), (2) a method for generating and applying an equalization filter from the measured hearing profile such that the application of the equalization filter to an audio signal played through the preferred listening device provides an equalized listening profile that recovers equal-loudness contours, and (3) a method for adapting the equalization filter coefficients generated from the measured hearing profile to higher or lower phon levels as the listening volume is adjusted by the listener.

Unlike adaptive equalization systems based on audiograms, which essentially attempt to characterize the listener's actual hearing thresholds and then set an equalization filter accordingly, adaptive, personalized equalization systems of exemplary embodiments of the present invention based on equal-loudness contours can account for the entire signal path from an audio signal source/player to the listener through a particular transduction/listening device in the actual listening environment. Therefore, the adaptive, personalized equalization provided by exemplary embodiments can compensate not just for the physical/perceptive listening capabilities of the listener but also for the effects that any media in the signal path have on the listening experience, such as the frequency response of the audio player/amplifier, attenuation caused by wiring or other transmission media (e.g., a wireless connection to the transduction/listening device), the frequency response of the transduction/listening device, acoustic properties of the listening environment, etc. Furthermore, rather than producing a single hearing profile for the listener as generally would be the case for a hearing test based on audiograms, embodiments of the present invention may produce different hearing profiles (and hence different equalization filters) for different combinations of audio players, transduction/listening devices, listening environments, etc. Thus, for example, different hearing profiles and equalization filters may apply when the listener uses different transduction/listening devices with a particular audio player.

Adaptive, Personalized Equalization System

Figure 1:
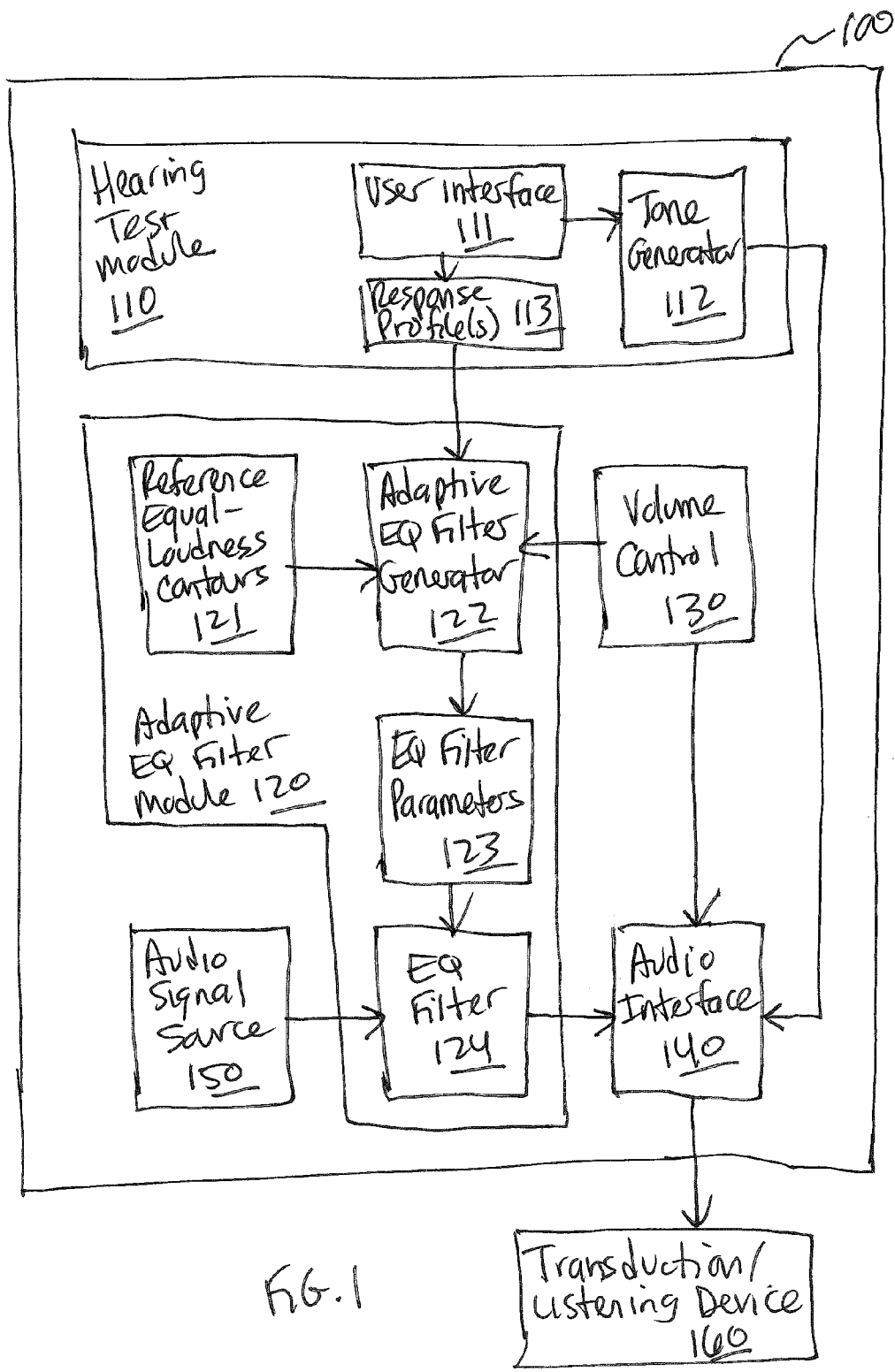
FIG. 1 is a schematic block diagram showing relevant components of a device 100 for adaptive, personalized equalization, in accordance with an exemplary embodiment of the present invention.

FIG. 1 is a schematic block diagram showing relevant components of a device 100 for adaptive, personalized equalization (referred to hereinafter as a "computational device"), in accordance with an exemplary embodiment of the present invention. Among other things, the computational device 100 includes a hearing test module 110, an adaptive equalization filter module 120, a volume control 130, an audio interface 140, and an audio signal source 150. Generally speaking, the hearing test module 110 performs an equal-loudness hearing test of the listener for a particular transduction/listening device 160 being used by the listener in the listening environment (e.g., in-the-ear earphones that seal the ear from external noise, earbuds that are placed in the ear but do not provide a seal, circumaural or over-the-ear devices, supra-aural or on-the ear devices, open-back devices, loudspeaker(s), or other device), and the adaptive equalization filter module 120 computes and applies an adaptive, personalized equalization filter based on the results of the hearing test and reference equal-loudness contours (e.g., ISO 226:2003 equal-loudness contours) for filtering an audio signal from the audio signal source 150 prior to presenting the audio signal to the listener through the transduction/listening device via the audio interface 140. Additionally or alternatively to controlling an output level of the audio interface 140, the volume control 130 (which may be, for example, a real or virtual knob, slider, button, or other control) also provides a volume level input to the adaptive equalization filter module 120, which, in certain embodiments, dynamically adapts the equalization filter based on the volume level selected by the listener, as discussed more fully below.

The computational device 100 may be a computer, cell phone, portable music player, tablet computer, laptop or notebook computer, desktop computer, stereo receiver, or any other programmable device, including a programmable device or module specific to a headset or listening device.

The audio signal source 150 may generate audio signals from any of a variety of sources internal to the device 100 and/or external to the device 100 (e.g., internal sources such as an MP3 player, DVD player, web browser, telephone; external sources such as might be connected to the device 100 by a wired or wireless communication connection).

The audio interface 140 may include an amplifier and a communication interface (e.g., a connector such as a headphone jack or speaker terminal, a wireless interface such as Bluetooth, etc.).

The transduction/listening device 160 (which may be referred to herein simply as the "listening device") includes at least one audio output device (e.g., loudspeaker or other transducer) and may include its own amplifier, volume control, and communication interface for interconnecting with the computational device 100 (alternatively, the transduction/listening device may be directly connected to the audio interface 140 of the computational device 100, such as by a wire, or may be integral to the computational device 100, such as a built-in speaker).

It should be noted that the present invention is not limited to any particular type of computational device, audio signal source, audio interface, or transduction/listening device.

Thus, the computational device 100 contains electronic elements and/or software required to perform the equal loudness hearing test used to establish the listener's hearing profile, to compute the equalization filter, and to perform the signal processing for applying the equalization filter to the audio signal to be reproduced. Conceptually, the hearing test module 110 includes a user interface 111 and a tone generator 112 and produces one or more response profiles 113 for the listener (which may be stored in a memory of the device 100), and the adaptive equalization filter module 120 includes stored reference equal-loudness contours 121, an adaptive equalization filter generator 122 that produces equalization filter parameters (e.g., including digital filter coefficients) 123, and an equalization filter 124 that filters the audio signal based on the equalization filter parameters 123. These modules are described in more detail below.

In a further embodiment, the computational device 100 may be used in conjunction with an electronics module (not shown in FIG. 1), which may contain one or more electronic components, digital signal processing devices, and/or microcontrollers that provide additional signal processing functionality, such as one-way or two-way radio communication, talk through, active noise reduction, in-ear voice pick-up, and/or impulse suppression. The electronics module may be programmable through the computational device 100 to incorporate the personalized equalization filter, and the electronics module may perform the filtering of audio signals through the equalization filter in conjunction with at least one additional signal processing function. Thus, the electronics module may be integral to the device 100 (e.g., part of the adaptive equalization filter module 120) or may be separate from the device 100. When separate from the device 100, the electronics module may be a stand-alone module that connects between the device 100 and the transduction/listening device, may be integral with the transduction/listening device, or may be part of another device in the signal path.

Figure 15:
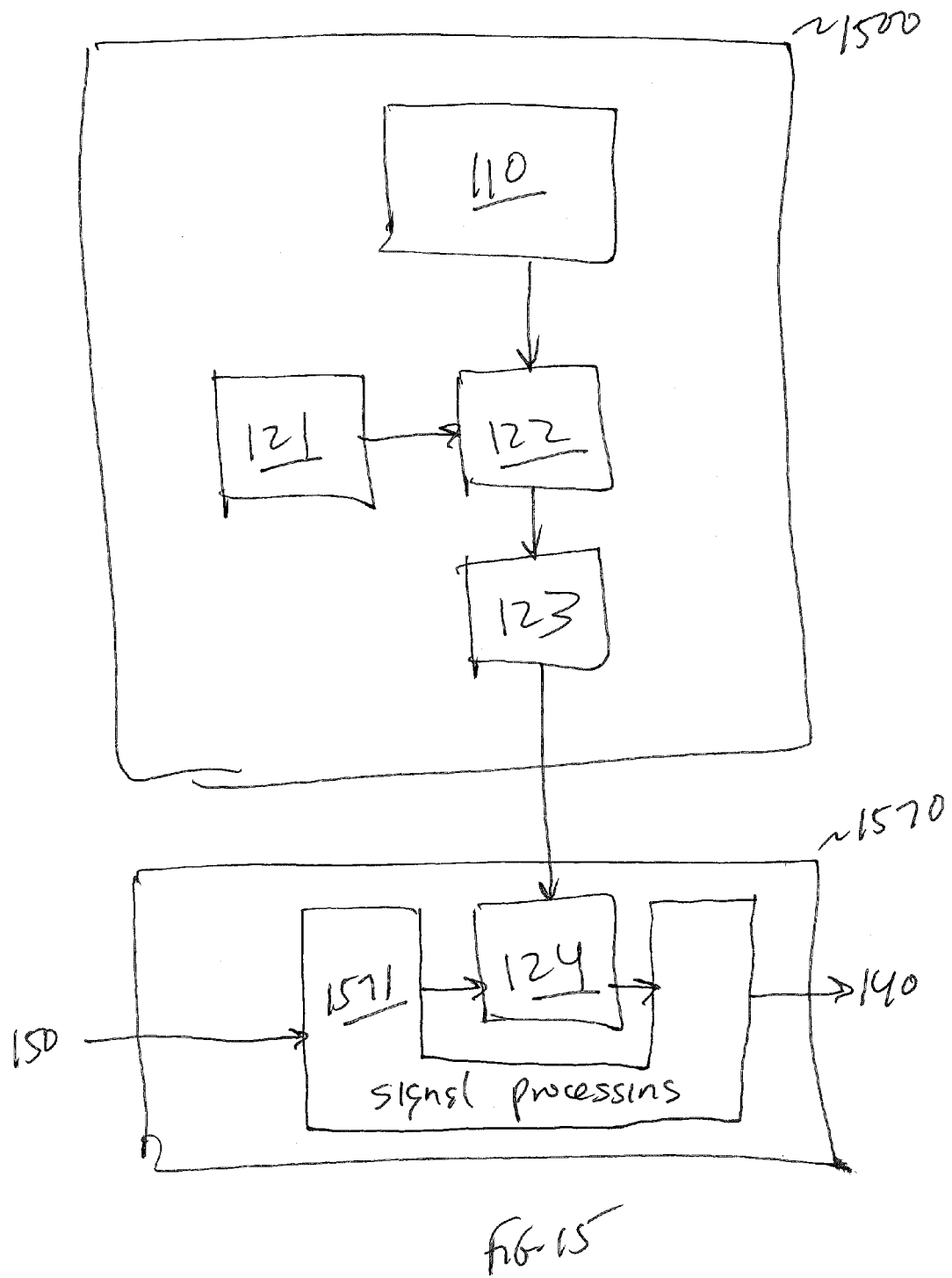
FIG. 15 is a schematic block diagram showing a computational device used in conjunction with a separate electronics module, in accordance with one exemplary embodiment.

FIG. 15 is a schematic block diagram showing a computational device used in conjunction with a separate electronics module, in accordance with one exemplary embodiment. In this example, a computational device 1500 including the hearing test module 110 and logic blocks 121-123 of the adaptive equalization filter module 120 operates in conjunction with a separate electronics module 1570 that includes logic block 124 of the adaptive equalization filter module 120 and further includes additional signal processing components 1571 that can be configured to process the audio signal before and/or after processing by the logic block 124. The additional signal processing components 1571 may include an electronic component for providing additional signal processing of the audio signal, a digital signal processor for providing additional signal processing of the audio signal, a microprocessor for providing additional signal processing of the audio signal, and/or other components. The additional signal processing functions provided by the additional signal processing components 1571 may include, without limitation, radio communication, talk-through, active noise reduction, in-ear voice pickup, and/or impulse suppression. The audio signal source 150 may be integral to the computational device 1500, integral to the electronics module 1570, or may be external. Similarly, the audio interface 140 may be integral to the computational device 1500 or may be integral to the electronics module 1570. Thus, for example, the electronics module 1570 may be an offload engine that performs signal processing functions, including application of the personalized equalization filter, and returns processed audio signals to the computational device 1500 for presentation to the listener, or the electronics module may be an intermediate device between the computational device 1500 and the listening device 160 or may be the listening device 160 itself.

It should be noted that the term "module" is used here to describe a logical association of components, which may include hardware and/or software components. Certain components (e.g., a microprocessor and its memories and other peripherals) may be shared by the module 110, the module 120, the electronics module, and/or other modules of the device 100 (e.g., a display driver, a web browser, etc.). Thus, for example, the hearing test module 110 and the adaptive equalization filter module 120 may include software that runs on a common microprocessor of the device 100.

Hearing Profile Generation

In exemplary embodiments, the listener's response profile 113 is measured in terms of its relationship to one or more reference equal-loudness contours 121, such as, for example, equal-loudness contours specified by ISO 226: 2003, which provide a measure of sound pressure as a function of signal frequency for which a listener perceives a constant loudness when presented with pure tones. Equal-loudness contours are derived through listening tests in which a listener compares the loudness of different tones and perceives the levels at which two tones separated by frequency to be of equal loudness. Equal-loudness contours are established in ISO 226:2003 through subjective experiments with a large population of normal-hearing subjects, and are averaged over subjects to establish "standard" curves.

The unit of measurement used to present equal-loudness contours is the phon. A phon is a unit of loudness level for pure tones that is used to compensate for the effect of frequency on the perceived loudness of tones, where 1 phon is equal to 1 dBSPL at a frequency of 1 KHz (i.e., a tone at 1000 Hz has a phon level equal to its sound pressure level in dB). An equal-loudness contour is a way of mapping the dBSPL of a pure tone to the perceived loudness level in phons. ISO 226:2003 is an internationally recognized set of equal-loudness contours which are used as reference equal-loudness contours in various embodiments of the present invention (although the present invention is not limited to any particular set of reference equal-loudness contours).

It is known that equal-loudness contours are themselves a function of phon level and thus are a function of listening volume setting. By measuring the response profile with respect to equal-loudness contours, a personalized, digital equalization filter is synthesized for the listener with respect to a particular transduction/listening device in the listening environment, which, when applied to an audio signal, provides an equalized audio signal that matches the equal-loudness profile for a given phon level as specified by the reference equal-loudness contour.

Figure 2:
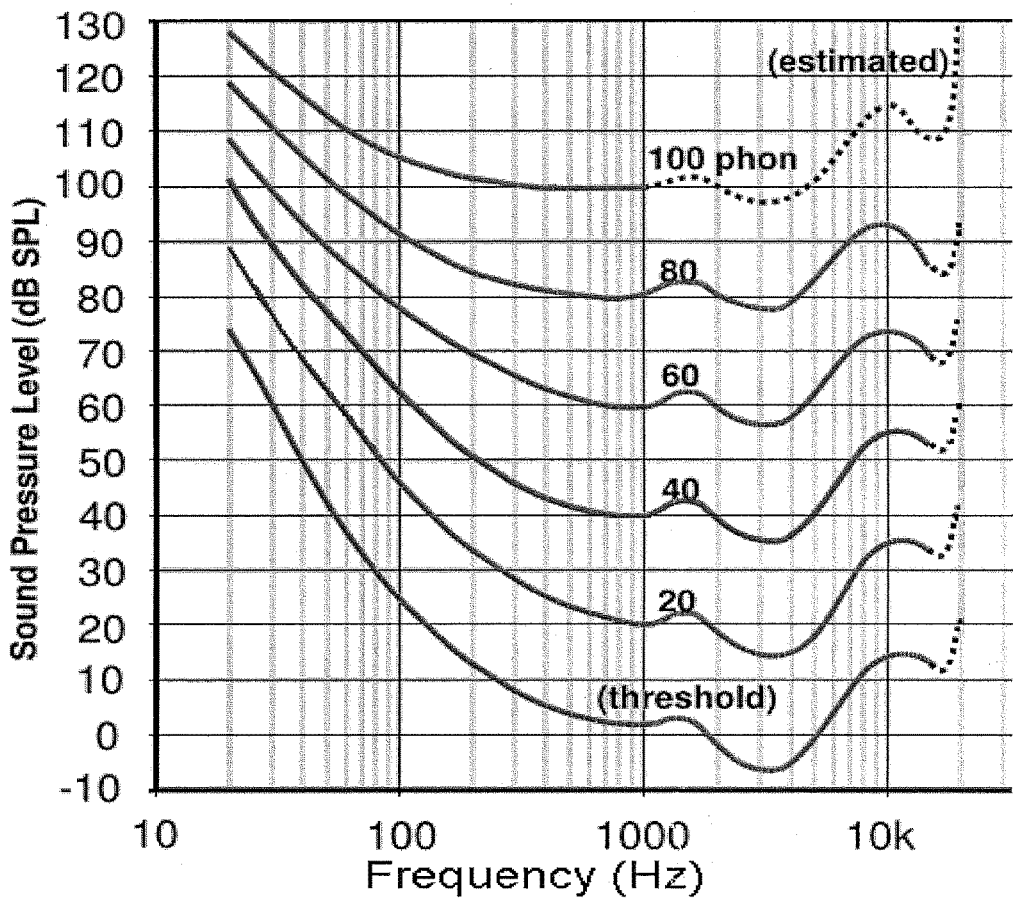
FIG. 2 shows equal-loudness contours from ISO 226: 2003 as known in the art.

FIG. 2 shows equal-loudness contours from ISO 226: 2003. As shown in FIG. 2, for a given phon level, a low frequency tone must be increased in dB level significantly for it to be perceived as equal loudness to a 1000 Hz tone, while sensitivity in the 4000 Hz band is higher. This phenomenon is largely attributed to the resonance of the ear canal and the structure of the middle ear. The audiogram or threshold test is equivalent to the equal-loudness "threshold" curve in FIG. 2.

Figure 3A:
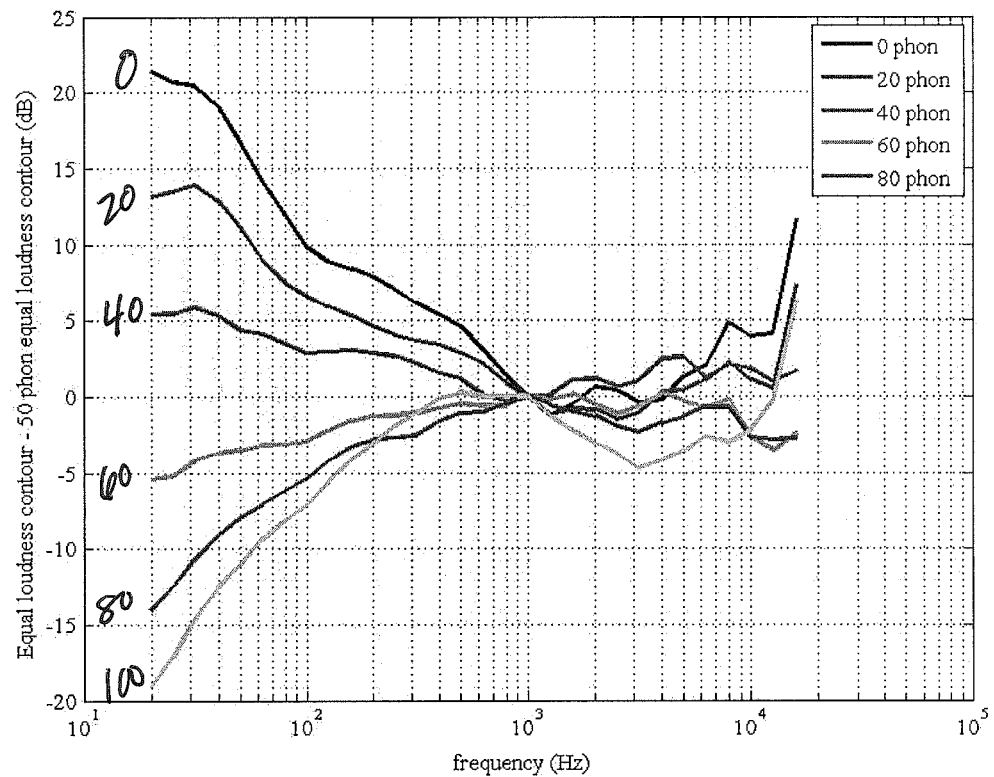
FIGS. 3A-3G show the difference between the equal-loudness contour at 50 phon and equal-loudness contours at threshold, 20, 40, 60, 80, and 100 phon.
Figure 3:
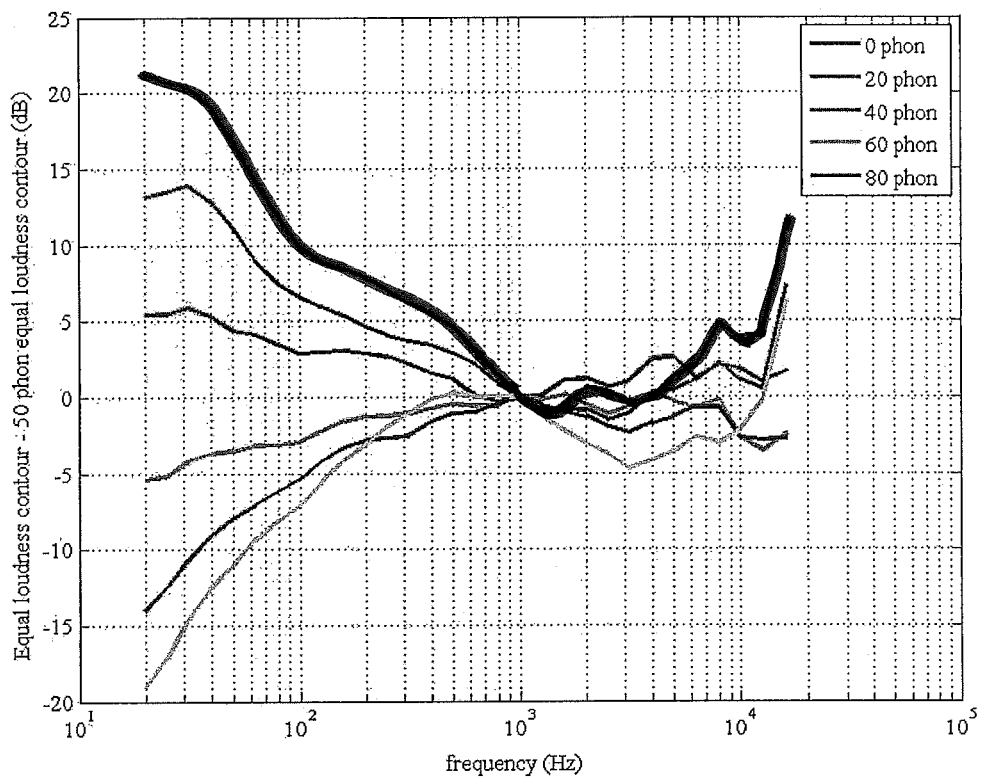
Figure 3C:
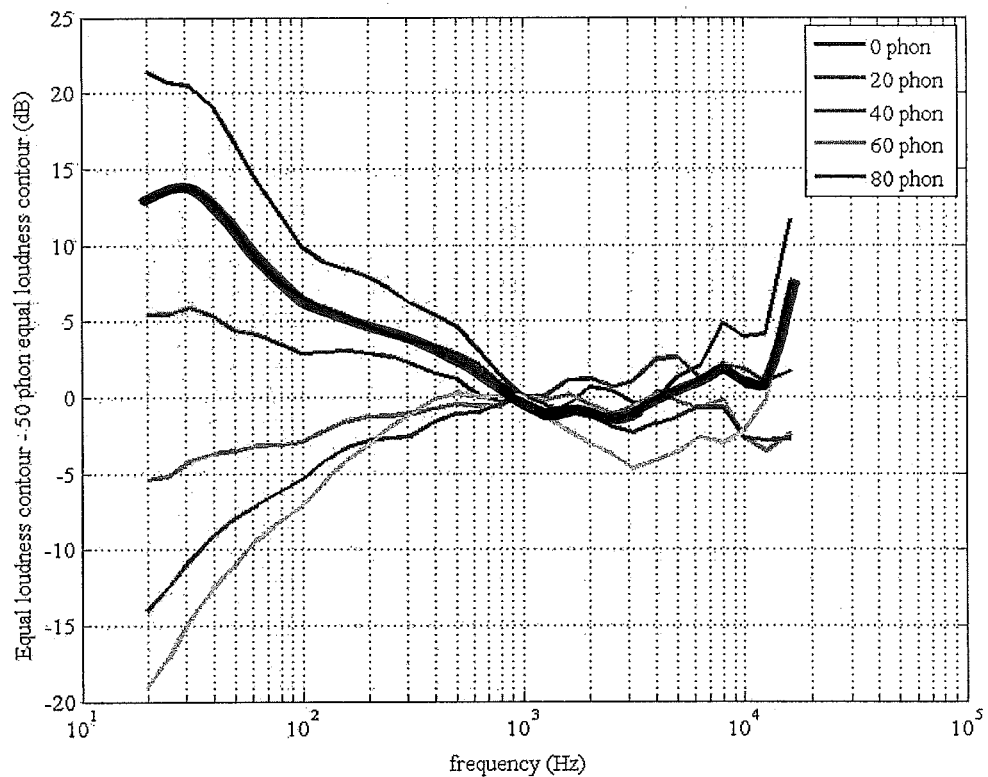
Figure 3D:
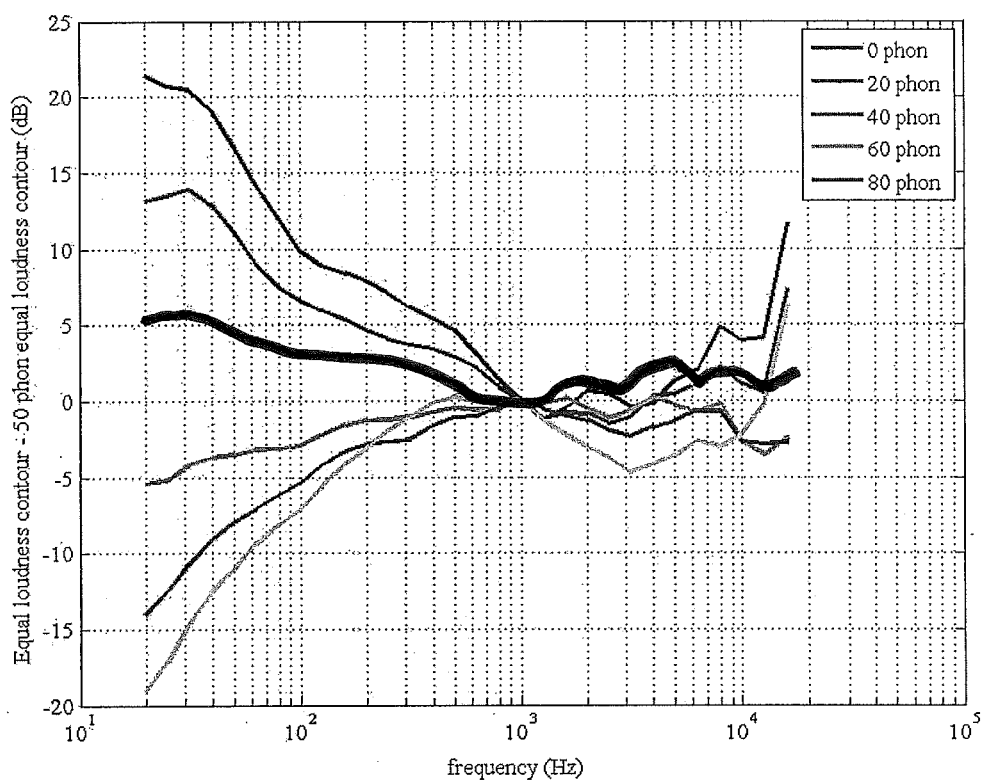
Figure 3E:
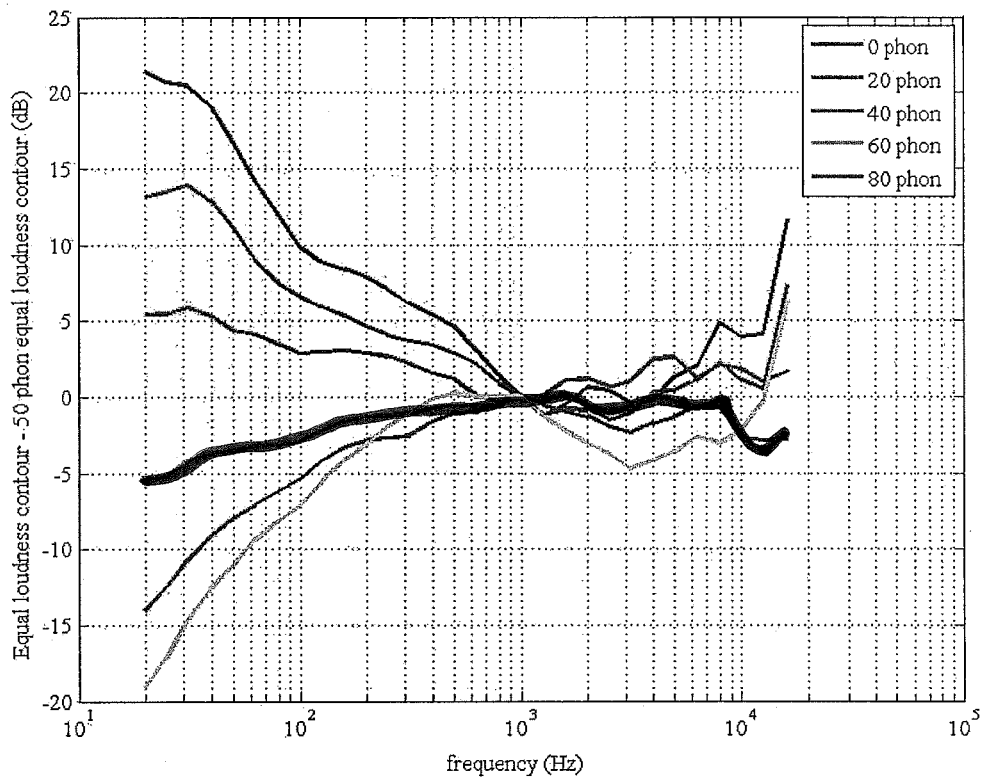
Figure 3F:
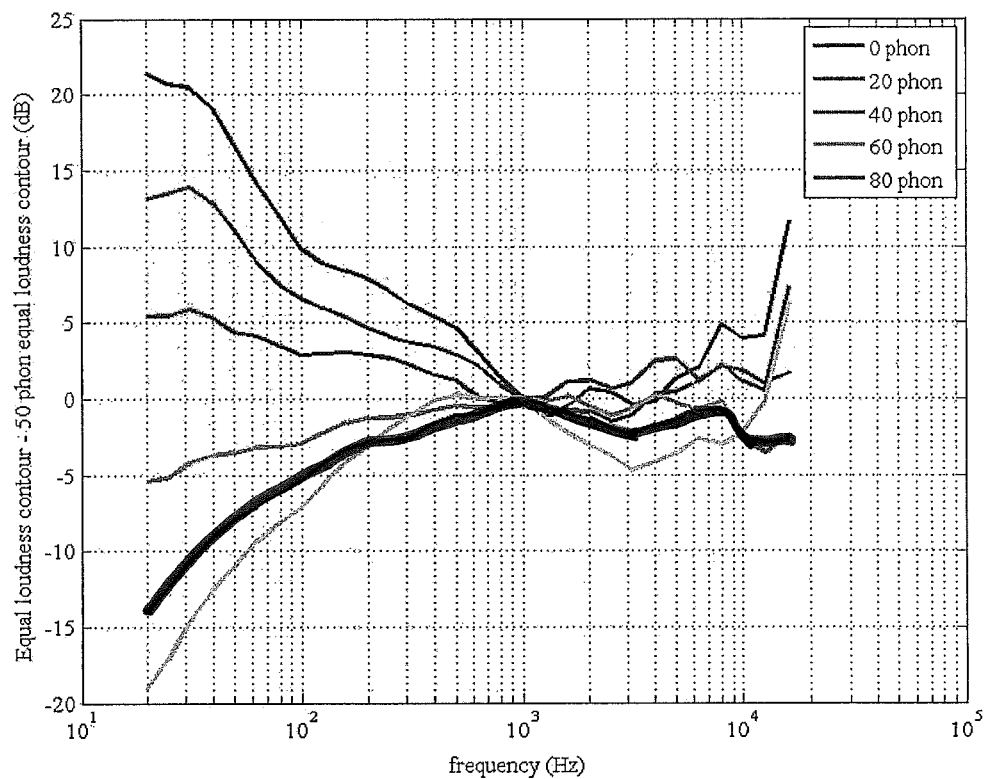
Figure 3G:
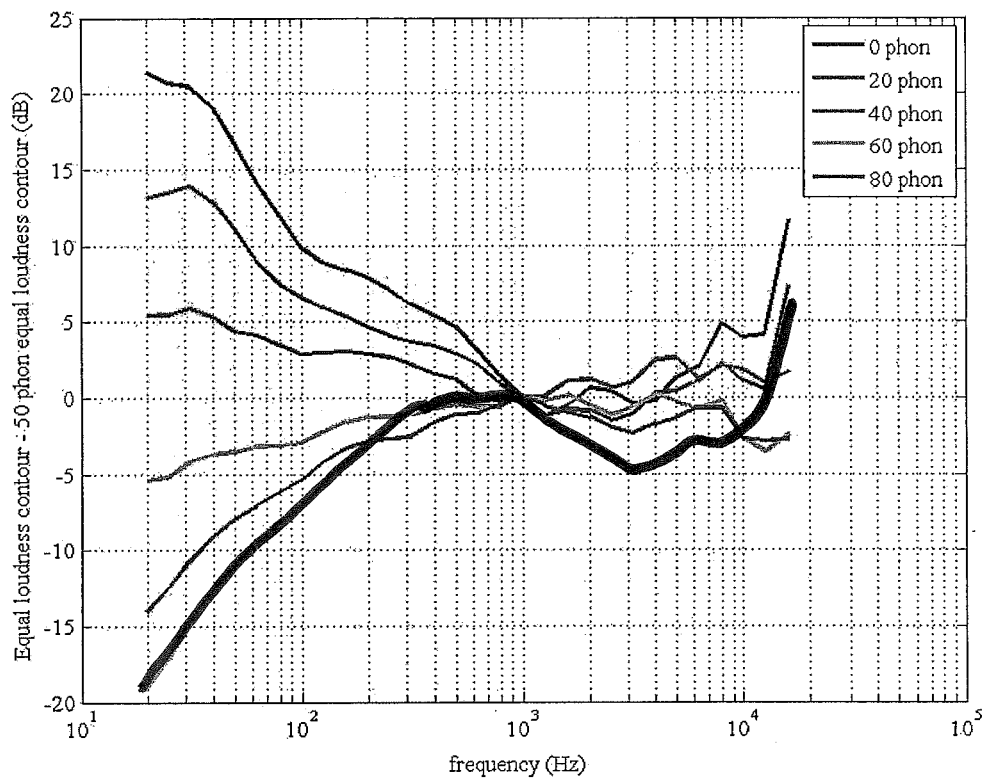

FIGS. 3A-3G show an example of the difference between the equal-loudness contour at 50 phon and equal-loudness contours at threshold (0), 20, 40, 60, 80, and 100 phon and demonstrates that the sensitivity of hearing depends on phon level. Specifically, FIG. 3A shows the plots for 0, 20, 40, 60, 80, and 100 phon overlayed. FIG. 3B highlights the 0 phon plot. FIG. 3C highlights the 20 phon plot. FIG. 3D highlights the 40 phon plot. FIG. 3E highlights the 60 phon plot. FIG. 3F highlights the 80 phon plot. FIG. 3G highlights the 100 phon plot.

In certain exemplary embodiments, the hearing test is performed generally as follows. With the listener listening through a particular transduction/listening device in a particular listening environment, the computational device 100, and, more particularly, the user interface 111 of the hearing test module 110 of the computation device 100, presents a user interface through which a set of test tones at frequencies within the audio band are presented to the listener and the listener can manually adjust and set the relative volume level of each test tone to a level at which the listener perceives all of the tones to be at the same loudness or other relationship chosen by the listener (e.g., if the listener prefers more or less of a particular tone, such as more or less bass or treble, then the user may purposely increase or reduce the loudness of that tone relative to the other tones). In the context of the present invention, a "set" includes one or more members, although the hearing test is generally performed using substantially more than one test tone (e.g., seventeen test tones). The computing device records the phon level set by the listener for each test tone in the response profile 113.

Figure 4:
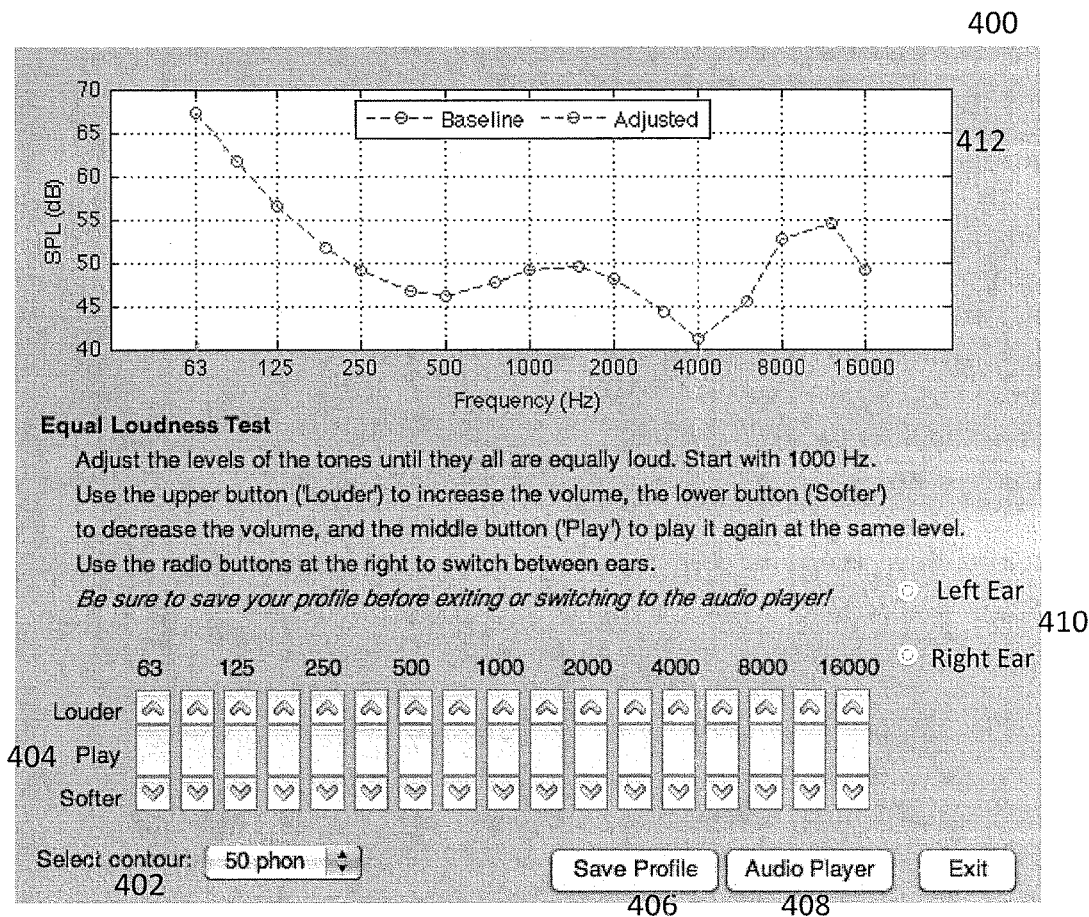
FIG. 4 is a schematic diagram of a graphical user interface for conducting the equal-loudness test, in accordance with one exemplary embodiment.

FIG. 4 is a schematic diagram of a graphical user interface 400 for conducting the equal-loudness test, in accordance with one exemplary embodiment. In this exemplary embodiment, the listener can select the reference equal-loudness contour for the hearing test via the "select contour" control 402 (in this example, a pull-down menu), and buttons 104 for playing and adjusting levels of individual tones are presented to measure hearing profile. The equal-loudness contour for a selected phon level (in this example, 50 phon) is shown graphically. In this exemplary embodiment, the listener is instructed to adjust the levels of the tones until they all are equally loud, starting with the 1000 Hz tone. The user sets the volume level of a 1000 Hz tone at a comfortable level, and volume level is recorded by the hearing test module 110. The sound pressure level in dB of the tone, given the volume setting, can be established, for example, based on a database containing the frequency response of common listening devices in testing using an ear simulator, such as a manikin having an in-ear microphone, establishing the phon level at which the hearing test is conducted. Once the volume is set for the 1000 Hz tone, the user plays additional tones, one at a time, from (in this example) 60 Hz to 16000 Hz and adjusts the volume of each tone to match the perceived loudness of the 1000 Hz tone. A graph 412 of the baseline (reference) contour and the adjusted values is displayed in this exemplary embodiment. The resulting sound pressure level vs. frequency plot, overlaid with the equal-loudness contour at the phon level at which the test is conducted, provide the deviation of the combined transfer function of the listening device and listener's auditory system from which a personalized equalization filter is derived. The listener saves the profile data at the conclusion of the test via the "save profile" control 406. It should be noted that the present invention is not limited to any particular user interface, to the order in which the test tones are played and adjusted, or to the specific test tones that are presented to the listener.

Based on the recorded phon levels recorded in the response profile 113 and a reference equal-loudness contour (e.g., an ISO 226:2003 equal-loudness contour) for the reference phon level, the computing device 100, and, more particularly, the adaptive equalization filter module 120, generates a personalized hearing profile for the listener, specifically by measuring, for each tone, the deviation of the recorded phon level from the corresponding phon level in the reference equal-loudness contour. The reference phon level may be selected by the listener as part of the test or may be established explicitly or implicitly as part of the test, e.g., the computing device may use the volume level input by the listener for a particular one of the tones (e.g., a 1000 Hz pure tone) as the reference phon level. Based on the hearing profile, the computing device synthesizes an equalization filter such that, when the filter is applied to the audio signal prior to presentation through the transduction/listening device (for example, when the listener invokes an audio player via the "audio player" control 408 of FIG. 4), the user's listening profile is adjusted to match the equal-loudness contour at the baseline phon level. In certain exemplary embodiments, once the equalization filter is created, small adjustments can be made manually in different bands based on user preference.

Figure 5:
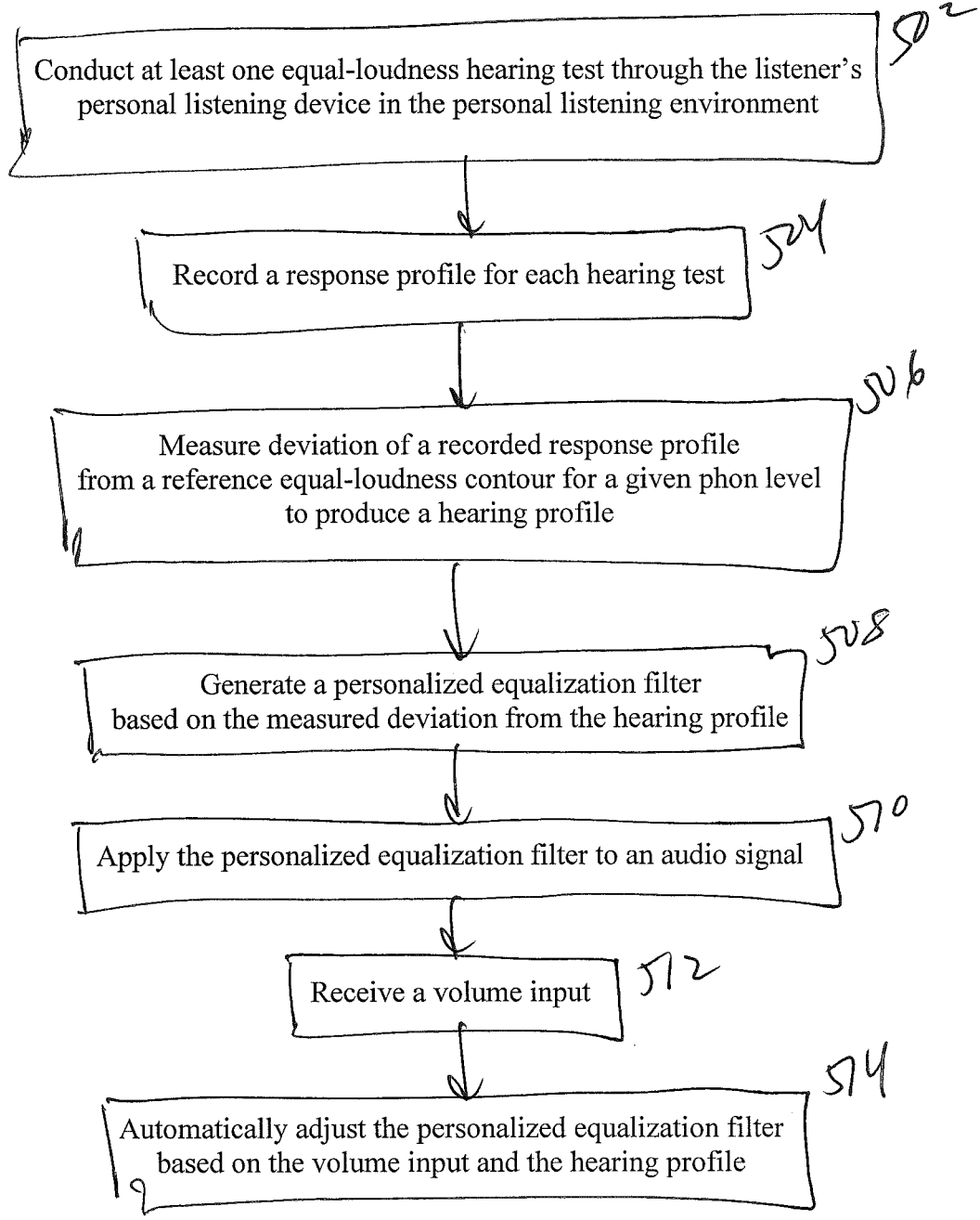
FIG. 5 shows a flow chart of one embodiment of the invention.

FIG. 5 is a logic flow diagram for adaptive, personalized equalization filtering, in accordance with various exemplary embodiments of the present invention. In block 502, at least one equal-loudness hearing test is conducted through the listener's personal listening device in the personal listening environment (as discussed below, multiple hearing tests may be used as part of the adaptive equalization filter generation). In block 504, a response profile is recorded for each hearing test. In block 506, deviation of a recorded response profile from a reference equal-loudness contour is measured for a given phon level to produce a hearing profile. In block 508, a personalized equalization filter is generated based on the measured deviation from the hearing profile. In block 510, the personalized equalization filter is applied to an audio signal. As discussed more fully below, a volume input may be received, in block 512, and the personalized equalization filter may be automatically adjusted based on the volume input and the hearing profile, in block 514.

Figure 6:
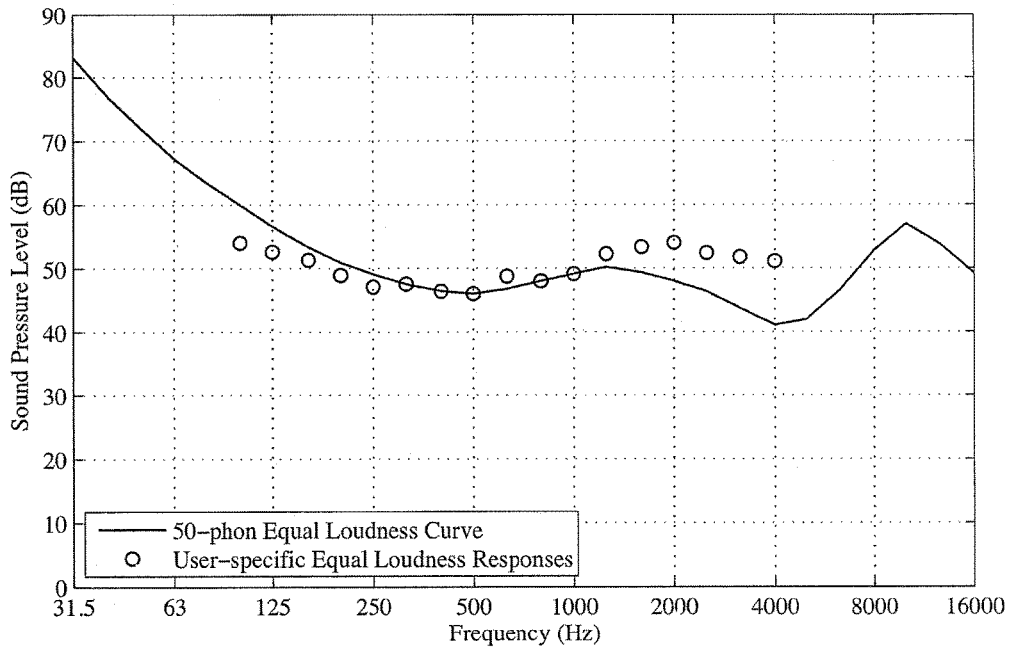
FIG. 6 shows an example of a measured equal-loudness contour for 50 phon overlaid with the ISO 226:2003 equal-loudness contour at 50 phon.

FIG. 6 shows an example of a measured equal-loudness contour for 50 phon overlaid with the ISO 226:2003 equal-loudness contour at 50 phon. In general, the equalization filter may require amplification of some frequencies, and attenuation of others.

It should be noted that, in certain embodiments, a separate hearing profile and filter may be generated for each ear of the listener (e.g., for listening through a stereo listening device such as headphones) or a hearing profile and filter may be generated for one ear of the listener (e.g., for listening through a mono listening device such as a Bluetooth earpiece). This generally would involve running the above-mentioned hearing profile generation process(es) twice, e.g., once in which the computing device generates tones and receives volume level inputs for the left ear while muting the audio signal to the right ear, and once in which the computing device generates tones and receives volume level inputs for the right ear while muting the audio signal to the left ear.

Thus, for example, as shown in FIG. 4, the user interface may include controls 410 (e.g., radio button) allowing the user to select a particular ear for the hearing test. The listener can perform a separate hearing test for each ear, and the adaptive equalization filter module 120 may generate and apply a separate equalization filter for each ear or alternatively may generate and apply a single aggregate equalization filter based on the response profiles for the two ears.

As discussed above, different hearing profiles (and hence different equalization filter coefficients) may be generated for a particular listener depending on the listening device being used by the listener, the computing device with which the listening device is used, the environment in which the listener is listening, and/or other factors. Thus, for example, a listener may use a particular computing device to generate personalized hearing profiles (and, therefore, personalized filters) for different types of listening devices that the listener uses with that computing device 100, such as one profile/filter for earbuds, one profile/filter for sound-canceling headphones, one profile/filter for audiophile headphones, one profile/filter for a Bluetooth headset, one profile/filter for amplified speakers, etc. The computing device 100 may allow the profile(s)/filter(s) to be stored for later selection by the listener so that the listener does not have to repeat the profile generation process each time the computing device is used, in which case the listener may be permitted to provide each profile with a name and/or other information (e.g., device type, listening environment, etc.). For example, when the user saves the response profile using the button 406 in FIG. 4, the hearing test module 110 may bring up a user interface screen that allows the listener to provide and save profile information such as, for example, a profile name, information regarding the transduction/listening device, information regarding the listening environment, etc. Thus, for example, the listener may have separate profiles/filters for such things as "Bluetooth headset in car," "sound-cancelling headset in airplane," "earbuds on subway," "speakers on patio," etc. Similarly, the device 100 and/or any applications running on the device 100 (e.g., audio player) may include controls allowing the listener to select and apply a saved profile/filter for a given audio listening session.

Figure 7:
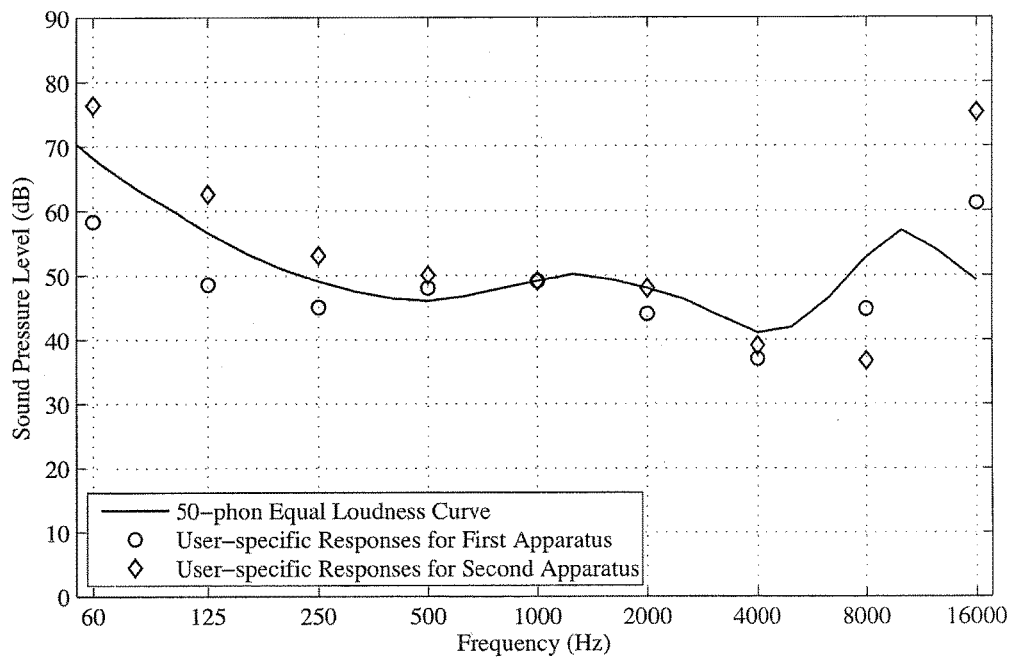
FIG. 7 shows examples of measured equal-loudness contours for one listener and two different listening devices.

FIG. 7 shows examples of equal loudness tests conducted using two different listening devices for the same listener and shows that the equalization required to match the 50 phon equal-loudness curve depends significantly on the listening device.

Adaptive Equalization Filter Generation

To create the equalization filter based on a response profile, the audio spectrum is divided into bands, and the difference between the listener's measured contour and the reference equal-loudness contour for the phon level at which the hearing test is conducted is used to generate an equalization filter for that band. In certain exemplary embodiments, a digital equalization filter is created using a set of parametric equalizing filters by automatically specifying the center frequency, bandwidth, and desired amplification or attenuation, given the difference between the listener's measured contour and the reference contour. Filters for each band are calculated and cascaded to provide the final equalization filter.

Because the perception of sound is dependent on volume, as the listener changes the volume level of the audio signal (e.g., using the volume control 130 of the computational device 100), certain embodiments of the present invention automatically adapt the filter coefficients based on the selected volume level. Since it generally would be impractical to produce a separate hearing profile (and hence a separate equalization filter) for each possible volume or phon level that the listener may choose, exemplary embodiments adaptively determine the equalization filter as a function of the audio volume or phon level that the listener chooses based on data from a limited number of hearing tests (e.g., one or two hearing tests).

In certain exemplary embodiments, the adaptive equalization filter generation is based on two hearing tests. Specifically, in addition to a first hearing test as discussed above, the listener performs all or part of a second hearing test at a second reference volume setting and thus a second reference phon level to establish a second hearing profile. Equalization filters for the two hearing profiles are generated. Subsequently, the coefficients of the equalization filter for each band are derived (e.g., through interpolation between known levels or extrapolation outside of known levels) and then the filters are cascaded to provide adaptive, personal equalization filters as a function of listening volume. Thus, when the volume of listening is changed, the equalization filter automatically adapts to match the equal-loudness contour of the new phon level.

Figure 13:
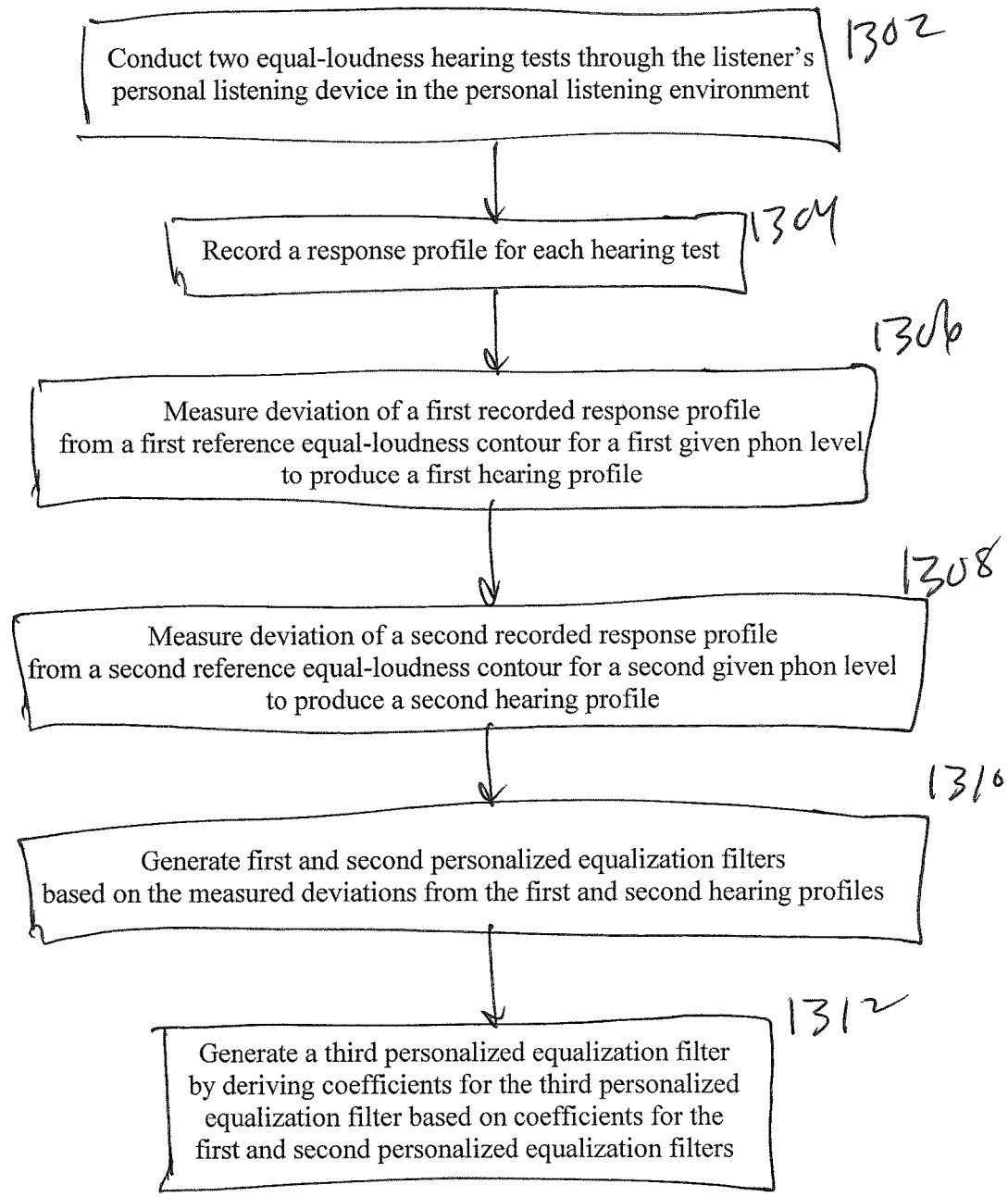
FIG. 13 is a logic flow diagram for adapting the personalized equalization filtering based on a change in volume selection, in accordance with a first exemplary embodiment.

FIG. 13 is a logic flow diagram for adapting the personalized equalization filtering based on a change in volume selection, in accordance with a first exemplary embodiment. Prior to receiving the volume change input, the listener will have conducted two equal-loudness hearing tests through the listener's personal listening device in the personal listening environment in block 1302, a response profile will have been recorded for each hearing test in block 1304, deviation of a first recorded response profile will have been measured from a first reference equal-loudness contour for a first given phon level to produce a first hearing profile in block 1306, deviation of a second recorded response profile will have been measured from a second reference equal-loudness contour for a second given phon level to produce a second hearing profile in block 1308, and first and second personalized equalization filters will have been generated based on the measured deviations from the first and second hearing profiles in block 1310. Upon receipt of the volume change input, then, a third personalized equalization filter is generated by deriving coefficients for the third personalized equalization filter based on coefficients for the first and second personalized equalization filters, in block 1312, such as by interpolation and/or extrapolation.

In certain exemplary embodiments, the adaptive equalization filter generation additionally or alternatively may be based on a single hearing test of the type described above. Specifically, the single equal-loudness listening test taken by the listener is used along with a numerical representation of the difference curves (e.g., as shown in FIG. 3) to determine the difference between the listener's loudness perception and equal-loudness contour at the phon level at which the listener conducted the test and at a different phon level corresponding to a different listening volume. The listening volume may be established, for example, based on a database containing the frequency response of common listening devices in testing using an ear simulator, such as a manikin having an in-ear microphone, establishing the phon level for the new listening volume. Equalization filters are computed for the new listening volume and the coefficients of the equalization filter for each band are derived and then the filters are cascaded to provide adaptive, personal equalization filters as a function of volume.

Figure 14:
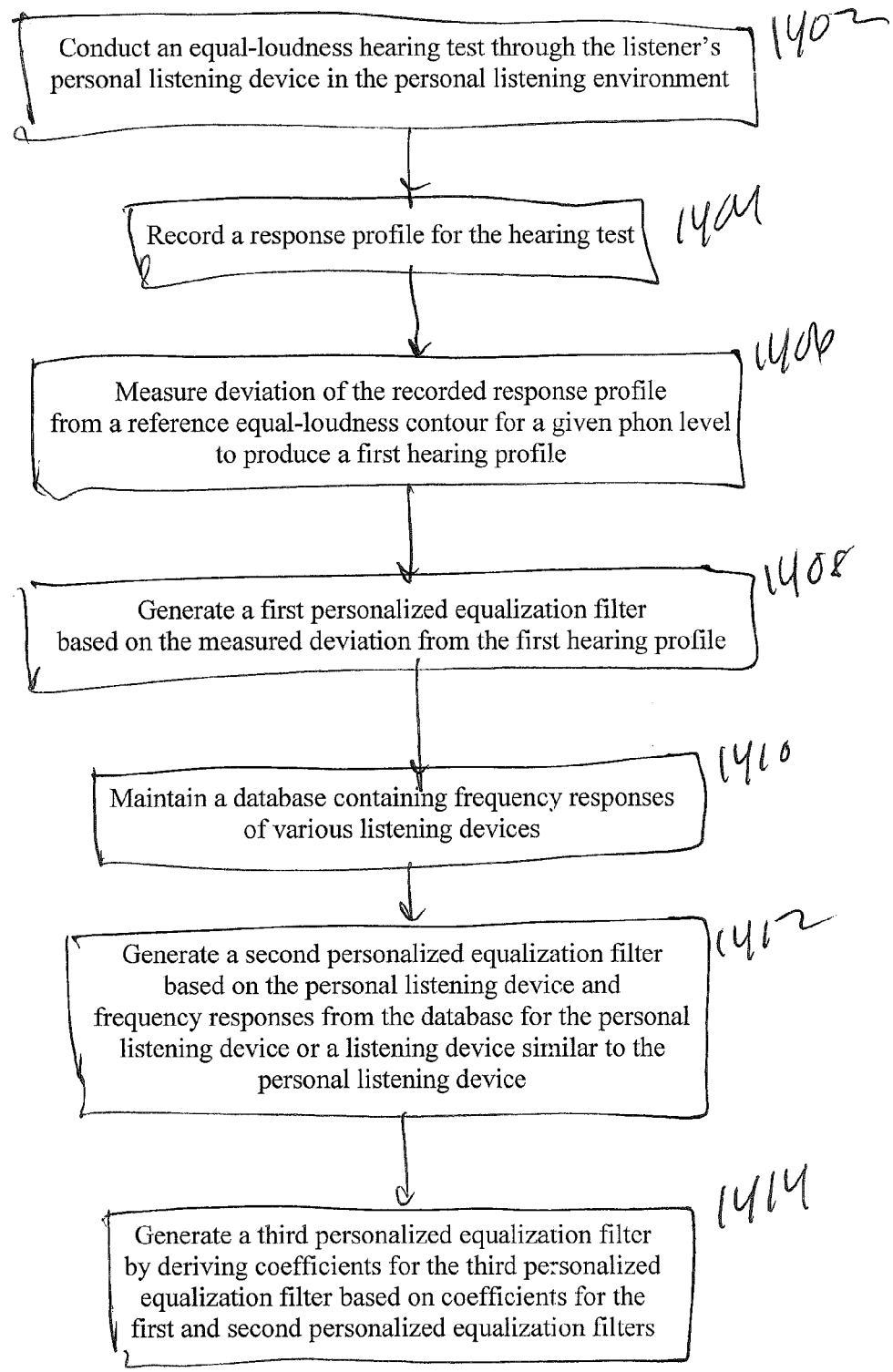
FIG. 14 is a logic flow diagram for adapting the personalized equalization filtering based on a change in volume selection, in accordance with a second exemplary embodiment.

FIG. 14 is a logic flow diagram for adapting the personalized equalization filtering based on a change in volume selection, in accordance with a second exemplary embodiment. Prior to receiving the volume change input, the listener will have conducted an equal-loudness hearing test through the listener's personal listening device in the personal listening environment in block 1402, a response profile will have been recorded for the hearing test in block 1404, deviation of the recorded response profile will have been measured from a reference equal-loudness contour for a given phon level to produce a first hearing profile in block 1406, and a first personalized equalization filter will have been generated based on the measured deviation from the first hearing profile. Furthermore, prior to receiving the volume change input, a database containing frequency responses of various listening devices is maintained in block 1410. Either prior to receiving the volume change input or upon receiving the volume change input, a second personalized equalization filter is generated based on the personal listening device and frequency responses from the database for the personal listening device or a listening device similar to the personal listening device, in block 1412. Then, a third personalized equalization filter is generated by deriving coefficients for the third personalized equalization filter based on coefficients for the first and second personalized equalization filters, in block 1414.

Figure 8:
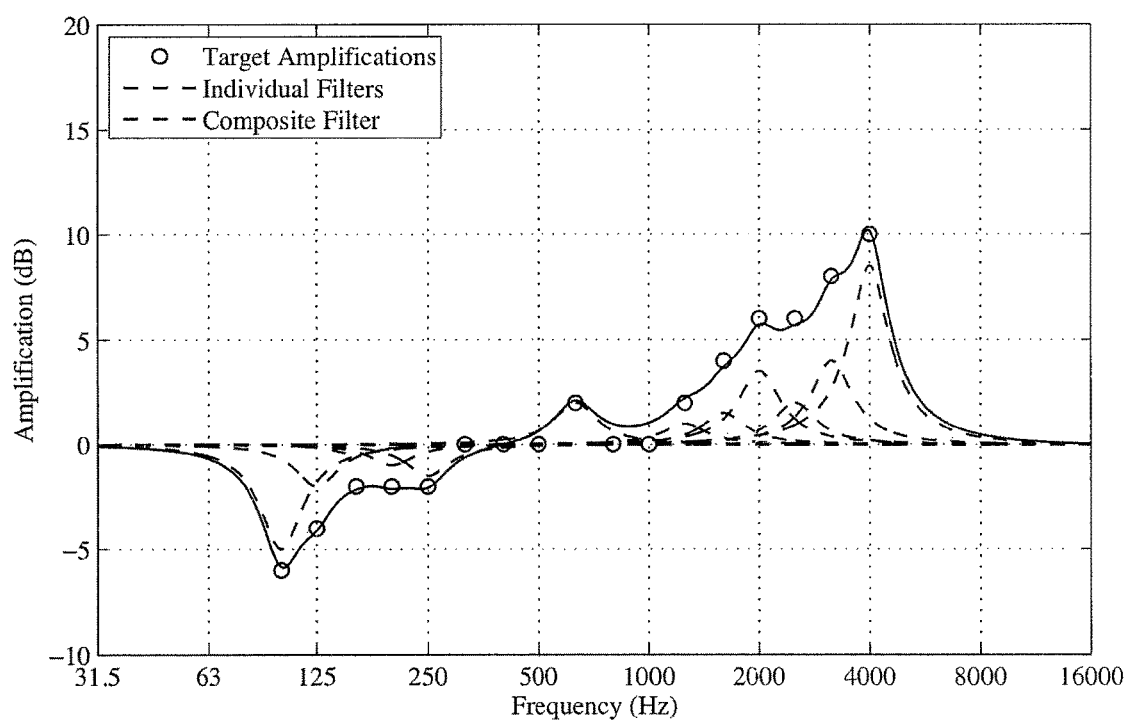
FIG. 8 shows a series of filters that when applied to a measured contour recovers an equal-loudness contour at a specified phon level.

FIG. 8 shows a series of filters that, when applied to a measured contour, recovers an equal-loudness contour at a specified phon level, in accordance with one example of adaptive, personalized equalization filtering of an exemplary embodiment of the present invention.

Figure 9:
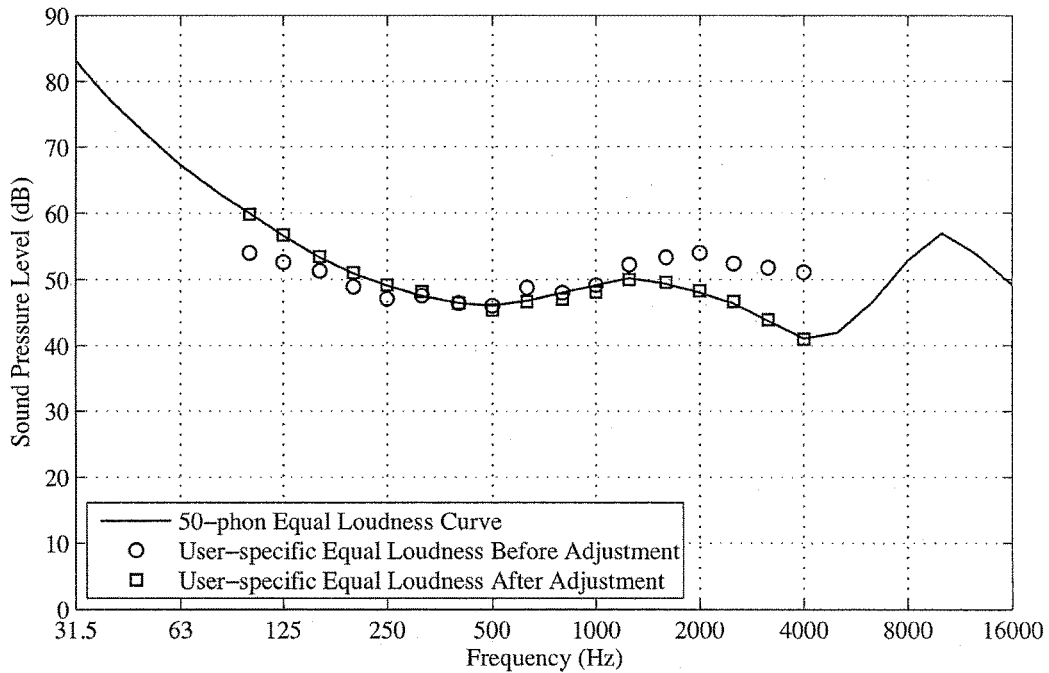
FIG. 9 shows the equal-loudness contour resulting from application of the equalization filter bank to the listener's measured hearing profile in conjunction with the ISO 226: 2003 50 phon equal-loudness contour.

FIG. 9 shows the equal-loudness contour resulting from application of the equalization filter bank to the listener's measured hearing profile in conjunction with the ISO 226:2003 50 phon equal-loudness contour, in accordance with one example of adaptive, personalized equalization filtering of an exemplary embodiment of the present invention.

Figure 10:
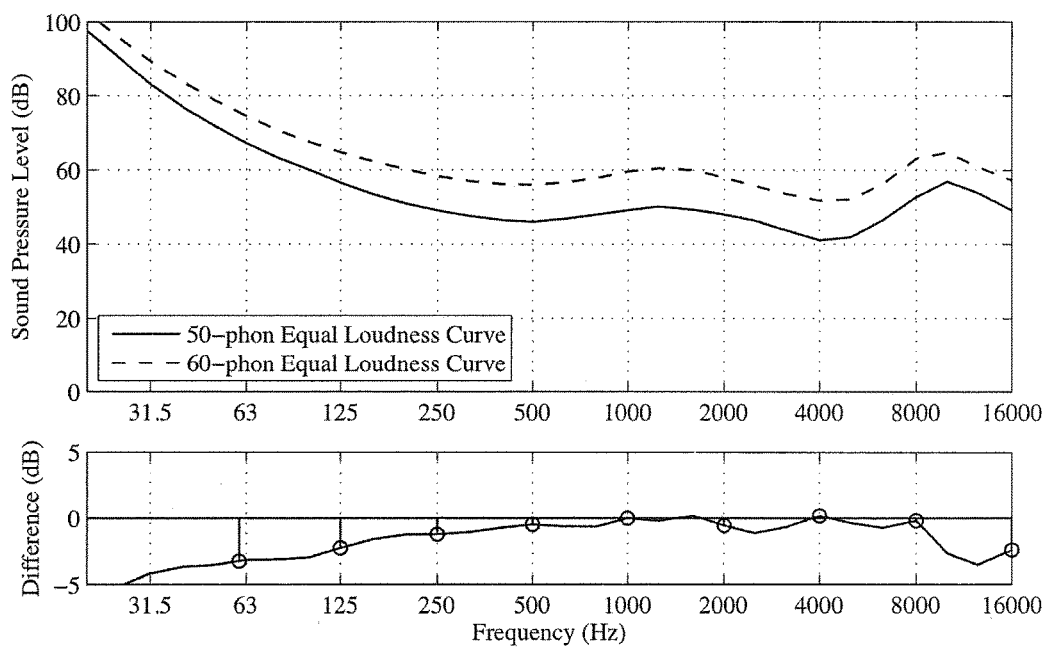
FIG. 10 shows the additional equalization necessary when moving from the 50 phon equal-loudness contour to the 60 phon equal-loudness contour.

FIG. 10 shows the additional equalization necessary when moving from the 50 phon equal-loudness contour to the 60 phon equal-loudness contour, in accordance with one example of adaptive, personalized equalization filtering of an exemplary embodiment of the present invention.

It should be noted that, in various alternative embodiments, the equalization filter may be adjusted in certain frequency bands to emphasize or de-emphasize the fidelity of certain audio signals, such as voice signals or a specific instrument in a song. Such adjustments may be made automatically by the adaptive equalization filter module 120 (e.g., the adaptive equalization filter module 120 may be configured specifically to emphasize or de-emphasize a particular frequency band or bands) or may be controlled manually by the listener, such as through a tone control or equalizer control that provides an input to the adaptive equalization filter module 120 for use by the adaptive equalization filter generator 122 in generating the equalization filter parameters 123.

It also should be noted that, in various alternative embodiments, the equalization filter may be adjusted to use head-related transfer functions to allow one or more audio signals to be perceived as coming from different directions in three dimensional space. A head-related transfer function (HRTF) is a frequency response, which can be modeled by a filter that shapes sound so that it is perceived to come from a certain direction. A pair of head-related transfer functions modeling how sound arrives at the ear from a specific point in space can be used to shape the audio signal so that it is perceived by the listener to come from that point in space. A collection of HRTFs can be used to create three-dimensional audio or surround sound. Head related transfer functions can be derived from measurements made in a laboratory environment as a ratio of 1) the measured frequency response at the listener's ear, and 2) the measured frequency response at the same point in space as the listener's ear when the listener is not present. Databases of average HRTFs over a population exist, allowing the creation of three-dimensional audio by playing an audio source through the HRTF. As is the case in traditional binaural audio presentation, the HRTF is affected by the frequency response of the playback device and listener's ear canal. Higher fidelity recreation of the environment is achieved by cascading the personalized equalization filter with a 3D audio or surround sound system comprised of head-related transfer functions.

Listening Device with Internal Microphone

Some listening devices (e.g., certain in-ear devices) include an internal microphone that can be used to characterize the transfer function associated with the "fit" of the listening device, i.e., due to the volume encapsulated between the listening device and the tympanic membrane. In such cases, the internal microphone can be used to assess the fit of the listening device, e.g., each time the user dons the device. The fit can be characterized to determine whether or not the fit has changed relative to the fit of the listening device that existed to generate a particular equalization filter (e.g., the fit of the listening device at the time the hearing test used to generate a particular equalization filter was performed, or the fit of the listening device at the time a particular equalization filter was tune or re-tuned). If the fit has changed, then the equalization filter may be adapted based on the current fit of the listening device, such as by re-tuning the equalization filter based on the transfer function associated with the current fit of the listening device and/or by prompting the user to redo the hearing test establish a new hearing profile and thus a new equalization filter based on the current fit of the listening device.

Figure 11:
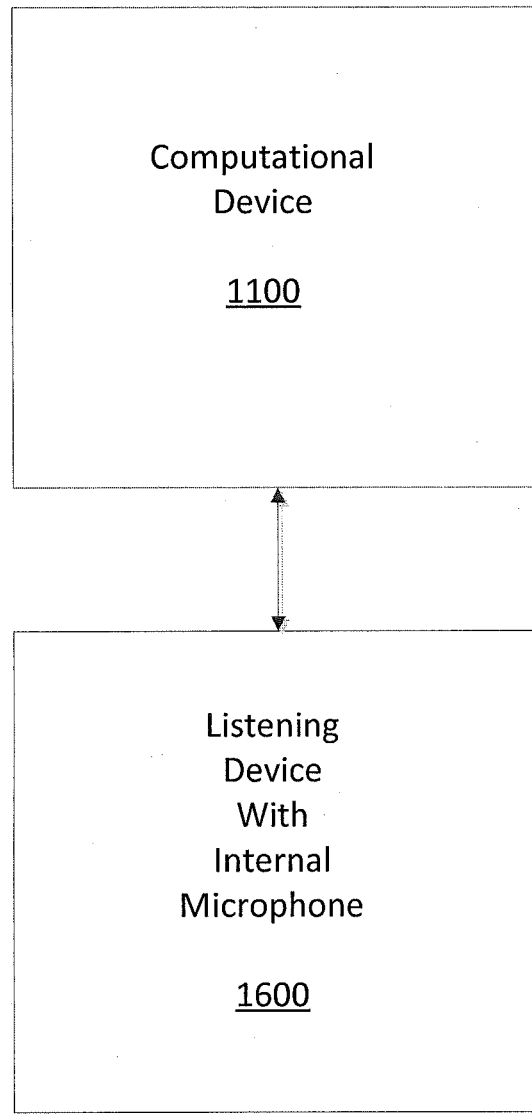
FIG. 11 is a schematic block diagram of a system having a computational device used in conjunction with a listening device having an internal microphone, in accordance with one exemplary embodiment.

FIG. 11 is a schematic block diagram of a system having a computational device 1100 used in conjunction with a listening device 1160 having an internal microphone, in accordance with one exemplary embodiment. Here, the computation device 1100 determines if the fit of the listening device 1600 has changed, e.g., based on audio signals or other signal received from the listening device 1600 (e.g., an indication from the listening device itself that the fit has changed) and automatically adapts the equalization filter based on the current fit of the listening device.

Figure 12:
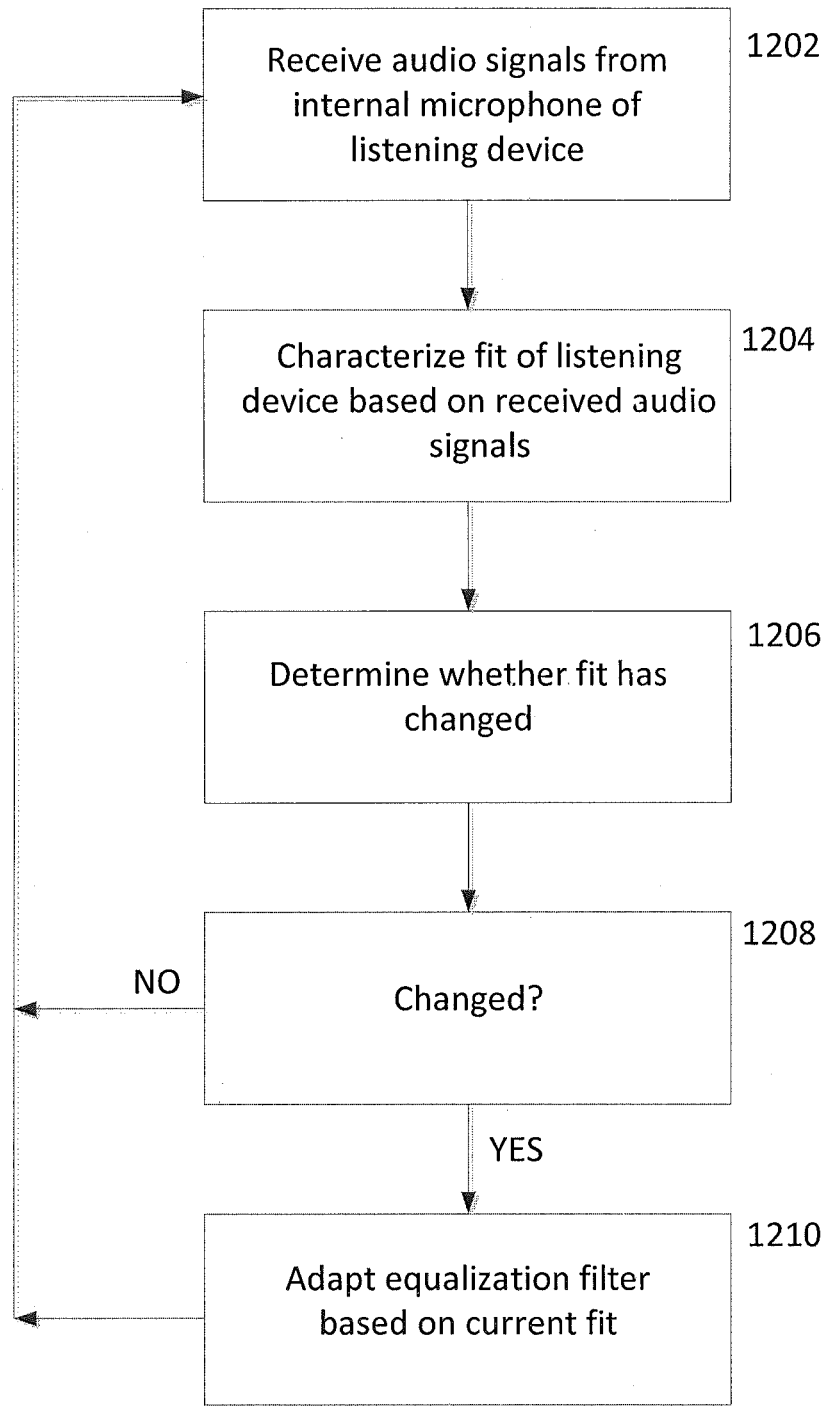
FIG. 12 is a logic flow diagram for adapting the personalized equalization filter based on the current fit of the listening device, e.g., by the computational device, in accordance with one exemplary embodiment.

FIG. 12 is a logic flow diagram for adapting the personalized equalization filter based on the current fit of the listening device, e.g., by the computational device 1100, in accordance with one exemplary embodiment. In block 1202, audio signals are received from the internal microphone of the listening device, e.g., by the computation device 1100 or other processing device (e.g., the listening device 1600, or perhaps the electronics module if present). In block 1204, the current fit of the listening device is characterized based on the received audio signals. In block 1206, a determination is made whether the fit has changed. If the fit has not changed (NO in block 1208), then the logic recycles to block 1202 to continue checking for a fit change. If the fit has changed (YES in block 1208), then the equalization filter is adapted based on the current fit of the listening device, and the logic recycles to block 1202 to check for another fit change.

Miscellaneous

It should be noted that arrows may be used in drawings to represent communication, transfer, or other activity involving two or more entities. Double-ended arrows generally indicate that activity may occur in both directions (e.g., a command/request in one direction with a corresponding reply back in the other direction, or peer-to-peer communications initiated by either entity), although in some situations, activity may not necessarily occur in both directions. Single-ended arrows generally indicate activity exclusively or predominantly in one direction, although it should be noted that, in certain situations, such directional activity actually may involve activities in both directions (e.g., a message from a sender to a receiver and an acknowledgement back from the receiver to the sender, or establishment of a connection prior to a transfer and termination of the connection following the transfer). Thus, the type of arrow used in a particular drawing to represent a particular activity is exemplary and should not be seen as limiting.

It should be noted that headings are used above for convenience and are not to be construed as limiting the present invention in any way.

It should be noted that terms such as "computational device" and "computer" may be used herein to describe devices that may be used in certain embodiments of the present invention and should not be construed to limit the present invention to any particular device type unless the context otherwise requires. Such devices typically include a processor (e.g., a microprocessor with memory and other peripherals and/or application-specific hardware) configured accordingly to perform device functions. Such devices may include one or more network interfaces for communicating over a communication network. Communication networks generally may include public and/or private networks; may include local-area, wide-area, metropolitan-area, storage, and/or other types of networks; and may employ communication technologies including, but in no way limited to, analog technologies, digital technologies, optical technologies, wireless technologies (e.g., Bluetooth), networking technologies, and internetworking technologies.

It should also be noted that devices may use communication protocols and messages (e.g., messages created, transmitted, received, stored, and/or processed by the device), and such messages may be conveyed by a communication network or medium. Unless the context otherwise requires, the present invention should not be construed as being limited to any particular communication message type, communication message format, or communication protocol. Thus, a communication message generally may include, without limitation, a frame, packet, datagram, user datagram, cell, or other type of communication message. Unless the context requires otherwise, references to specific communication protocols are exemplary, and it should be understood that alternative embodiments may, as appropriate, employ variations of such communication protocols (e.g., modifications or extensions of the protocol that may be made from time-to-time) or other protocols either known or developed in the future.

It should also be noted that logic flows may be described herein to demonstrate various aspects of the invention, and should not be construed to limit the present invention to any particular logic flow or logic implementation. The described logic may be partitioned into different logic blocks (e.g., programs, modules, functions, or subroutines) without changing the overall results or otherwise departing from the true scope of the invention. Often times, logic elements may be added, modified, omitted, performed in a different order, or implemented using different logic constructs (e.g., logic gates, looping primitives, conditional logic, and other logic constructs) without changing the overall results or otherwise departing from the true scope of the invention.

The present invention may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof. Computer program logic implementing some or all of the described functionality is typically implemented as a set of computer program instructions that is converted into a computer executable form, stored as such in a computer readable medium, and executed by a microprocessor under the control of an operating system. Hardware-based logic implementing some or all of the described functionality may be implemented using one or more appropriately configured FPGAs.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

Computer program logic implementing all or part of the functionality previously described herein may be executed at different times on a single processor (e.g., concurrently) or may be executed at the same or different times on multiple processors and may run under a single operating system process/thread or under different operating system processes/threads. Thus, the term "computer process" refers generally to the execution of a set of computer program instructions regardless of whether different computer processes are executed on the same or different processors and regardless of whether different computer processes run under the same operating system process/thread or different operating system processes/threads.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web). Of course, some embodiments of the invention may be implemented as a combination of both software (e.g., a computer program product) and hardware. Still other embodiments of the invention are implemented as entirely hardware, or entirely software.

The present invention may be embodied in other specific forms without departing from the true scope of the invention, and numerous variations and modifications will be apparent to those skilled in the art based on the teachings herein. Any references to the "invention" are intended to refer to exemplary embodiments of the invention and should not be construed to refer to all embodiments of the invention unless the context otherwise requires. The described embodiments are to be considered in all respects only as illustrative and not restrictive.

What is claimed is:

1. A method for automatically generating a personalized equalization filter for listener, the method comprising:

measuring a first hearing profile of the listener as a deviation of a first recorded response profile, obtained from a first equal loudness hearing test when the listener is listening through a personal listening device in a personal listening environment, from a first reference equal-loudness contour associated with a first given phon level;

automatically generating a first personalized equalization filter based on the measured deviation of the first hearing profile such that application of the personalized equalization filter to an audio signal played through the personal listening device provides an equalized listening profile that recovers the equal-loudness contour for which the hearing profile was measured;

applying the first personalized equalization filter to an audio signal played through the personal listening device; and automatically adapting the personalized equalization filter to a new phon level that differs from the phon level for which the listener's hearing profile was measured so that the personalized equalization filter automatically adapts to match an equal-loudness contour of the new phon level, wherein automatically adapting the personalized equalization filter to a new phon level that differs from the phon level for which the listener's hearing profile was measured comprises:

automatically adapting the personalized equalization filter based on a second recorded response profile and a second reference equal-loudness contour associated with a second given phon level, wherein automatically adapting the personalized equalization filter based on the second recorded response profile and the second reference equal-loudness contour associated with the second given phon level comprises:

measuring a second hearing profile of the listener as a deviation of the second recorded response profile from the second reference equal-loudness contour;

automatically generating a second personalized equalization filter based on the measured deviation of the first hearing profile; and generating a third personalized equalization filter by deriving coefficients for the third personalized equalization filter based on coefficients for the first and second personalized equalization filters.

2. A method according to claim 1, wherein measuring the first hearing profile of the listener comprises:

conducting a first equal loudness hearing test including presenting a user interface to the listener, the user interface providing a first set of test tones and allowing the listener to adjust and set the relative volume level of each test tone to a level at which the listener perceives all of the tones to be at the same loudness for the first given phon level;

recording a phon level set by the listener for each test tone to produce the first recorded response profile; and measuring the hearing profile of the listener as a deviation of the first recorded response profile from the reference equal-loudness contour at the first given phon level.

3. A method according to claim 2, wherein the first equal loudness hearing test is conducted in a manner that does not require a quiet environment with low noise floor.

4. A method according to claim 1, wherein automatically generating the first personalized equalization filter comprises:

automatically creating a first digital equalization filter using a set of parametric equalizing filters by automatically specifying the center frequency, bandwidth, and desired amplification or attenuation, based on the difference between the equal-loudness contour for which the hearing profile was measured and the reference equal-loudness contour at the given phon level and cascading filters for each band to provide a personalized equalization filter.

5. A method according to claim 1, wherein the reference equal-loudness contour is an equal-loudness contour specified by ISO 226:2003.

6. A method according to claim 1, wherein automatically adapting the personalized equalization filter to a new phon level that differs from the phon level for which the listener's hearing profile was measured comprises: automatically adapting the personalized equalization filter based on a database containing frequency responses of various listening devices.

7. A method according to claim 1, further comprising:

automatically adjusting the personalized equalization filter based on a head-related transfer function to allow one or more audio signals to be perceived as coming from different directions in three dimensional space.

8. A method according to claim 1, further comprising:

automatically adjusting the personalized equalization filter to emphasize or de-emphasize audio signals within a specified band.

9. A method according to claim 1, wherein the personal listening device includes an internal microphone for determining a fit of the personal listening device on the listener, and, upon determining that the fit of the personal listening device on the listener has changed, the method further comprises at least one of: automatically adjusting the personalized equalization filter based on a transfer function associated with the fit of the device; or automatically prompting the listener to conduct a hearing test due to the change in fit.

10. Apparatus for automatically generating a personalized equalization filter for a listener, the apparatus comprising:

a hearing test module configured to produce a first recorded response profile from a first equal loudness hearing test when the listener is listening through a personal listening device in a personal listening environment; and an adaptive equalization filter module configured to measure a first hearing profile of the listener as a deviation of the first recorded response profile from a first reference equal-loudness contour associated with a first given phon level, automatically generate a first personalized equalization filter based on the measured deviation of the first hearing profile such that application of the personalized equalization filter to an audio signal played through the personal listening device provides an equalized listening profile that recovers the equal-loudness contour for which the hearing profile was measured, and apply the first personalized equalization filter to an audio signal played through the personal listening device, wherein the adaptive equalization filter module is further configured to automatically adapt the personalized equalization filter to a new phon level that differs from the phon level for which the listener's hearing profile was measured so that the personalized equalization filter automatically adapts to match an equal-loudness contour of the new phon level, wherein the adaptive equalization filter module is configured to automatically adapt the personalized equalization filter based on a second recorded response profile and a second reference equal-loudness contour associated with a second given phon level, and wherein the adaptive equalization filter module is configured to measure a second hearing profile of the listener as a deviation of the second recorded response profile from the second reference equal-loudness contour, automatically generate a second personalized equalization filter based on the measured deviation of the first hearing profile, and generate a third personalized equalization filter by deriving coefficients for the third personalized equalization filter based on coefficients for the first and second personalized equalization filters.

11. The apparatus according to claim 10, wherein the hearing test module is configured to:

conduct a first equal loudness hearing test including presenting a user interface to the listener, the user interface providing a first set of test tones and allowing the listener to adjust and set the relative volume level of each test tone to a level at which the listener perceives all of the tones to be at the same loudness for the first given phon level; and record a phon level set by the listener for each test tone to produce the first recorded response profile.

12. The apparatus according to claim 11, wherein the hearing test module is configured to conduct the first equal loudness hearing test in a manner that does not require a quiet environment with low noise floor.

13. The apparatus according to claim 10, wherein the adaptive equalization filter module is configured to automatically generate the first personalized equalization filter by automatically creating a first digital equalization filter using a set of parametric equalizing filters by automatically specifying the center frequency, bandwidth, and desired amplification or attenuation, based on the difference between the equal-loudness contour for which the hearing profile was measured and the reference equal-loudness contour at the given phon level and cascading filters for each band to provide a personalized equalization filter.

14. The apparatus according to claim 10, wherein the reference equal-loudness contour is an equal-loudness contour specified by ISO 226:2003.

15. The apparatus according to claim 10, wherein the adaptive equalization filter module is configured to automatically adapt the personalized equalization filter based on a database containing frequency responses of various listening devices.

16. The apparatus according to claim 10, wherein the adaptive equalization filter module is further configured to automatically adjust the personalized equalization filter based on a head-related transfer function to allow one or more audio signals to be perceived as coming from different directions in three dimensional space.

17. The apparatus according to claim 10, wherein the adaptive equalization filter module is further configured to automatically adjust the personalized equalization filter to emphasize or de-emphasize audio signals within a specified band.

18. The apparatus according to claim 10, wherein the personal listening device includes an internal microphone for determining a fit of the personal listening device on the listener, and wherein at least one of:
- the adaptive equalization filter module is further configured to automatically adjust the personalized equalization filter based on a transfer function associated with the fit of the device upon determining that the fit of the personal listening device on the listener has changed; or
- the adaptive equalization filter module is further configured to automatically prompt the listener to conduct a hearing test due to the change in fit upon determining that the fit of the personal listening device on the listener has changed.

19. The apparatus according to claim 10, wherein the hearing test module and the adaptive equalization filter module are integral to a device including at least one of a computer, cell phone, portable music player, tablet computer, laptop computer, notebook computer, desktop computer, stereo receiver, or programmable device.

20. The apparatus according to claim 10, wherein the hearing test module and an adaptive equalization filter generator of the adaptive equalization filter module are integral to a first device and wherein an equalization filter of the adaptive equalization filter module is integral to a second device used in conjunction with the first device, the second device including at least one component providing additional signal processing of the audio signal, the second device being programmable through the first device to incorporate the personalized equalization filter and apply the personalized equalization filter to the audio signal in conjunction with at least one additional signal processing function.

21. The apparatus according to claim 20, wherein the second device includes at least one of:
- an electronic component for providing additional signal processing of the audio signal;
- a digital signal processor for providing additional signal processing of the audio signal; or
- a microprocessor for providing additional signal processing of the audio signal.

22. The apparatus of claim 20, wherein the additional signal processing function includes at least one of:
- radio communication;
- talk-through;
- active noise reduction;
- in-ear voice pickup; or
- impulse suppression.

* * * * *